United States Patent
Narendranath et al.

(10) Patent No.: US 9,663,807 B2
(45) Date of Patent: May 30, 2017

(54) SYSTEMS AND METHODS FOR HYDROLYSIS OF BIOMASS

(75) Inventors: Neelakantam V. Narendranath, Sioux Falls, SD (US); William F. McDonald, Utica, OH (US); Jason Alan Bootsma, Sioux Falls, SD (US)

(73) Assignee: POET RESEARCH, INC., Sioux Falls, SD (US)

(*) Notice: Subject to any disclaimer, the term of this patent is extended or adjusted under 35 U.S.C. 154(b) by 355 days.

(21) Appl. No.: 13/980,255

(22) PCT Filed: Jan. 18, 2012
(Under 37 CFR 1.47)

(86) PCT No.: PCT/US2012/021731
§ 371 (c)(1),
(2), (4) Date: Apr. 3, 2014

(87) PCT Pub. No.: WO2012/099967
PCT Pub. Date: Jul. 26, 2012

(65) Prior Publication Data
US 2014/0234911 A1    Aug. 21, 2014

Related U.S. Application Data

(60) Provisional application No. 61/433,864, filed on Jan. 18, 2011.

(51) Int. Cl.
| | | |
|---|---|---|
| C12M 1/00 | (2006.01) | |
| C12P 19/14 | (2006.01) | |
| C12P 7/10 | (2006.01) | |
| C12P 19/02 | (2006.01) | |
| C13K 1/02 | (2006.01) | |

(52) U.S. Cl.
CPC ............ *C12P 19/14* (2013.01); *C12M 21/12* (2013.01); *C12M 43/02* (2013.01); *C12M 45/04* (2013.01); *C12M 45/06* (2013.01); *C12P 7/10* (2013.01); *C12P 19/02* (2013.01); *C13K 1/02* (2013.01); *C12P 2201/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | |
|---|---|---|
| 3,212,932 A | 10/1965 | Hess et al. |
| 4,014,743 A | 3/1977 | Black |
| 4,029,515 A | 6/1977 | Kiminki et al. |
| 4,152,197 A | 5/1979 | Lindahl et al. |
| 4,168,988 A | 9/1979 | Riehm et al. |
| 4,342,831 A | 8/1982 | Faber et al. |
| 4,425,433 A | 1/1984 | Neves |
| 4,427,453 A | 1/1984 | Reitter |
| 4,432,805 A | 2/1984 | Nuuttila et al. |
| 4,461,648 A | 7/1984 | Foody |
| 4,529,699 A | 7/1985 | Gerez et al. |
| 4,552,616 A | 11/1985 | Kauppi |
| 4,612,286 A | 9/1986 | Sherman et al. |
| 4,668,340 A | 5/1987 | Sherman |
| 4,752,579 A | 6/1988 | Arena et al. |
| 4,908,098 A | 3/1990 | DeLong et al. |
| 4,941,944 A | 7/1990 | Chang |
| 4,997,488 A | 3/1991 | Gould et al. |
| 5,125,977 A | 6/1992 | Grohmann et al. |
| 5,171,592 A | 12/1992 | Holtzapple et al. |
| 5,221,357 A | 6/1993 | Brink |
| 5,328,562 A | 7/1994 | Rafferty et al. |
| 5,338,366 A | 8/1994 | Grace et al. |
| 5,366,558 A | 11/1994 | Brink |
| 5,370,999 A | 12/1994 | Stuart |
| 5,411,594 A | 5/1995 | Brelsford |
| 5,424,417 A | 6/1995 | Torget et al. |
| 5,498,766 A | 3/1996 | Stuart et al. |

(Continued)

FOREIGN PATENT DOCUMENTS

| | | |
|---|---|---|
| EP | 0 044 658 | 1/1982 |
| EP | 0 098 490 | 1/1984 |
| EP | 0 159 795 | 10/1985 |
| EP | 0 884 391 | 12/1998 |
| EP | 1 259 466 | 11/2002 |
| EP | 1 130 085 | 10/2005 |
| FR | 2 397 486 | 2/1979 |
| FR | 2 609 046 | 7/1988 |
| WO | WO 94/08027 | 4/1994 |
| WO | WO 94/29475 | 12/1994 |

(Continued)

OTHER PUBLICATIONS

Adney, B. et al., "Measurement of Cellulase Activities", Technical Report NREL/TP-510-42628 (2008) Cover; p. 1-8.
Caparros, S. et al., "Xylooligosaccharides Production from Arundo donax", J. Agric. Food Chem. 55 (2007): p. 5536-5543.
Cort, J. et al., "Minimize Scale-Up Risk", www.aiche.org/cep, (2010): p. 39-49.
Demain, A.L. et al., "Cellulase, Clostridia, and Ethanol", Microbiology and Molecular Biology Reviews 69(1) (2005): p. 124-154.

(Continued)

*Primary Examiner* — Soren Harward
*Assistant Examiner* — Paul D. Pyla
(74) *Attorney, Agent, or Firm* — Kagan Binder, PLLC

(57) ABSTRACT

Systems and methods are disclosed for treating lignocellulosic biomass to be supplied to a fermentation system for production of a fermentation product. The systems and methods comprise pre-treating the biomass into pre-treated biomass and separating the pre-treated biomass into a liquid component comprising sugars and a solids component comprising cellulose and lignin. The systems and methods also comprise treating the solids component of the pre-treated biomass into a treated component. The biomass comprises lignocellulosic material. Treating the solids component comprises application of an enzyme formulation and makeup water to form a slurry. The enzyme formulation comprises a cellulase enzyme. The makeup water includes a clarified thin stillage composition and/or an anaerobic membrane digester effluent composition.

20 Claims, 17 Drawing Sheets

(56) References Cited

U.S. PATENT DOCUMENTS

| | | | |
|---|---|---|---|
| 5,536,325 A | 7/1996 | Brink | |
| 5,562,777 A | 10/1996 | Farone et al. | |
| 5,580,389 A | 12/1996 | Farone et al. | |
| 5,597,714 A | 1/1997 | Farone et al. | |
| 5,628,830 A | 5/1997 | Brink | |
| 5,693,296 A | 12/1997 | Holtzapple et al. | |
| 5,705,369 A | 1/1998 | Torget et al. | |
| 5,711,817 A | 1/1998 | Titmas | |
| 5,726,046 A | 3/1998 | Farone et al. | |
| 5,733,758 A | 3/1998 | Nguyen | |
| 5,769,934 A | 6/1998 | Ha et al. | |
| 5,782,982 A | 7/1998 | Farone et al. | |
| 5,820,687 A | 10/1998 | Farone et al. | |
| 5,865,898 A | 2/1999 | Holtzapple et al. | |
| 5,879,463 A | 3/1999 | Proenca | |
| 5,916,780 A | 6/1999 | Foody et al. | |
| 5,932,452 A | 8/1999 | Mustranta et al. | |
| 5,932,456 A | 8/1999 | Van Draanen et al. | |
| 5,972,118 A | 10/1999 | Hester et al. | |
| 5,975,439 A | 11/1999 | Chieffalo et al. | |
| 6,022,419 A | 2/2000 | Torget et al. | |
| 6,090,595 A | 7/2000 | Foody et al. | |
| 6,228,177 B1 | 5/2001 | Torget | |
| 6,379,504 B1 | 4/2002 | Miele et al. | |
| 6,419,788 B1 | 7/2002 | Wingerson | |
| 6,423,145 B1 | 7/2002 | Nguyen et al. | |
| 6,555,350 B2 | 4/2003 | Ahring et al. | |
| 6,620,292 B2 | 9/2003 | Wingerson | |
| 6,660,506 B2 | 12/2003 | Nguyen et al. | |
| 6,692,578 B2 | 2/2004 | Schmidt et al. | |
| 6,770,168 B1 | 8/2004 | Stigsson | |
| 7,198,925 B2 | 4/2007 | Foody | |
| 7,238,242 B2 | 7/2007 | Pinatti et al. | |
| 7,354,743 B2 | 4/2008 | Vlasenko et al. | |
| 7,455,997 B2 | 11/2008 | Hughes | |
| 7,501,025 B2 | 3/2009 | Bakker et al. | |
| 7,503,981 B2 | 3/2009 | Wyman et al. | |
| 7,585,652 B2 | 9/2009 | Foody et al. | |
| 7,604,967 B2 | 10/2009 | Yang et al. | |
| 7,649,086 B2 | 1/2010 | Belanger et al. | |
| 7,666,637 B2 | 2/2010 | Nguyen | |
| 7,670,813 B2 | 3/2010 | Foody et al. | |
| 7,709,042 B2 | 5/2010 | Foody et al. | |
| 7,754,456 B2 | 7/2010 | Penttila et al. | |
| 7,754,457 B2 | 7/2010 | Foody et al. | |
| 7,807,419 B2 | 10/2010 | Hennessey et al. | |
| 7,815,741 B2 | 10/2010 | Olson | |
| 7,815,876 B2 | 10/2010 | Olson | |
| 7,819,976 B2 | 10/2010 | Friend et al. | |
| 7,875,444 B2 | 1/2011 | Yang et al. | |
| 7,901,511 B2 | 3/2011 | Griffin et al. | |
| 8,057,639 B2 | 11/2011 | Pschorn et al. | |
| 8,057,641 B2 | 11/2011 | Bartek et al. | |
| 8,110,383 B2 | 2/2012 | Jönsson et al. | |
| 8,123,864 B2 | 2/2012 | Christensen et al. | |
| 8,288,600 B2 | 10/2012 | Bartek et al. | |
| 8,449,728 B2 | 5/2013 | Redford | |
| 8,815,552 B2 | 8/2014 | Narendranath et al. | |
| 2002/0192774 A1 | 12/2002 | Ahring et al. | |
| 2004/0060673 A1 | 4/2004 | Phillips et al. | |
| 2004/0252580 A1 | 12/2004 | Nagy et al. | |
| 2005/0069998 A1 | 3/2005 | Ballesteros Perdices et al. | |
| 2006/0188965 A1 | 8/2006 | Wyman et al. | |
| 2006/0281157 A1 | 12/2006 | Chotani et al. | |
| 2008/0026431 A1 | 1/2008 | Saito et al. | |
| 2008/0057555 A1 | 3/2008 | Nguyen | |
| 2008/0277082 A1 | 11/2008 | Pschorn et al. | |
| 2008/0295981 A1 | 12/2008 | Shin et al. | |
| 2009/0035826 A1* | 2/2009 | Tolan | B01D 3/001 435/99 |
| 2009/0042259 A1* | 2/2009 | Dale | C12P 19/14 435/105 |
| 2009/0093027 A1* | 4/2009 | Balan | C12P 7/10 435/99 |
| 2009/0098616 A1 | 4/2009 | Burke et al. | |
| 2009/0308383 A1 | 12/2009 | Shin et al. | |
| 2010/0003733 A1 | 1/2010 | Foody et al. | |
| 2010/0144001 A1 | 6/2010 | Horton | |
| 2010/0233771 A1 | 9/2010 | McDonald et al. | |
| 2010/0285553 A1 | 11/2010 | Delmas et al. | |
| 2011/0011391 A1* | 1/2011 | Burke | C08B 1/00 127/1 |
| 2011/0079219 A1 | 4/2011 | McDonald et al. | |
| 2011/0094505 A1 | 4/2011 | Bulla et al. | |
| 2011/0171708 A1 | 7/2011 | Larsen | |
| 2012/0129234 A1 | 5/2012 | McDonald et al. | |
| 2012/0138246 A1 | 6/2012 | Christensen et al. | |
| 2012/0201947 A1 | 8/2012 | Stuart | |
| 2013/0065289 A1 | 3/2013 | Carlson | |
| 2013/0143290 A1 | 6/2013 | Narendranath | |
| 2013/0337521 A1 | 12/2013 | Carlson et al. | |
| 2014/0024826 A1 | 1/2014 | Narendranath et al. | |
| 2014/0209092 A1 | 7/2014 | McDonald et al. | |
| 2015/0037859 A1 | 2/2015 | Bootsma | |
| 2015/0072390 A1 | 3/2015 | Narendranath et al. | |
| 2015/0128932 A1 | 5/2015 | Kwiatkowski et al. | |

FOREIGN PATENT DOCUMENTS

| | | |
|---|---|---|
| WO | WO 95/08648 | 3/1995 |
| WO | WO 98/14270 | 4/1998 |
| WO | WO 98/56958 | 12/1998 |
| WO | WO 99/06133 | 2/1999 |
| WO | WO 00/14120 | 3/2000 |
| WO | WO 00/61858 | 10/2000 |
| WO | WO 00/73221 | 12/2000 |
| WO | WO 01/32715 | 5/2001 |
| WO | WO 01/60752 | 8/2001 |
| WO | WO 02/14598 | 2/2002 |
| WO | WO 02/24882 | 3/2002 |
| WO | WO 02/38786 | 5/2002 |
| WO | WO 02/051561 | 7/2002 |
| WO | WO 02/067691 | 9/2002 |
| WO | WO 02/070753 | 9/2002 |
| WO | WO 03/013714 | 2/2003 |
| WO | WO 03/071025 | 8/2003 |
| WO | WO 03/078644 | 9/2003 |
| WO | WO 2004/081193 | 9/2004 |
| WO | WO 2005/099854 | 10/2005 |
| WO | WO 2005/118828 | 12/2005 |
| WO | WO 2006/032282 | 3/2006 |
| WO | WO 2006/034590 | 4/2006 |
| WO | WO 2006/056838 | 6/2006 |
| WO | WO 2006/101832 | 9/2006 |
| WO | WO 2007/009463 | 1/2007 |
| WO | WO 2008/095098 | 8/2008 |
| WO | WO 2008/131229 | 10/2008 |
| WO | WO 2009/003167 | 12/2008 |
| WO | WO 2009/045651 | 4/2009 |
| WO | WO 2009/108773 | 9/2009 |
| WO | WO 2010/071805 | 6/2010 |
| WO | WO 2010/113129 | 10/2010 |
| WO | WO 2010/113130 | 10/2010 |
| WO | WO 2011/061400 | 5/2011 |
| WO | WO 2011/116317 | 9/2011 |
| WO | WO 2011/159915 | 12/2011 |
| WO | WO 2012/042497 | 4/2012 |
| WO | WO 2012/042498 | 4/2012 |
| WO | WO 2012/103281 | 8/2012 |
| WO | WO 2012/131665 | 10/2012 |

OTHER PUBLICATIONS

Dien, B.S. et al., "Enzyme characterization for hydrolysis of AFEX and liquid hot-water pretreated distillers' grains and their conversion to ethanol", Bioresource Technology 99 (2008): p. 5216-5225.

Gibbons, W.R. et al., "Fuel Ethanol and High Protein Feed from Corn and Corn-Whey Mixtures in a Farm-Scale Plant", Biotechnology and Bioengineering XXV (1983): p. 2127-2148.

Goodman, B. J., "FY 1988 Ethanol from Biomass Annual Report" (1989): p. 1-458.

(56) References Cited

OTHER PUBLICATIONS

Grohmann, K. et al., "Optimization of Dilute Acid Pretreatment of Biomass", Biotechnology and Bioengineering Symp. 15 (1985): p. 59-80.

Grohmann, K. et al., "Dilute Acid Pretreatment of Biomass at High Solids Concentrations", Biotechnology and Bioengineering Symp. 17 (1986): p. 135-151.

Humbird, D. et al., "Process Design and Economics for Biochemical Conversion of Lignocellulosic Biomass to Ethanol: Dilute-Acid Pretreatment and Enzymatic Hydrolysis of Corn Stover", National Renewable Energy Laboratory (2011): Covers with Introduction; p. 1-114.

Jeoh, T. "Steam Explosion Pretreatment of Cotton Gin Waste for Fuel Ethanol Production", Thesis submitted to Virginia Polytechnic Institute and State University (1998): Cover with Introduction; p. 1-138.

Jorgensen, H. et al., "Enzymatic conversion of lignocellulose into fermentable sugars: challenges and opportunities", Biofuels, Bioprod. Bioref. 1 (2001): p. 119-134.

Kumar, R. et al., "Effect of Enzyme Supplementation at Moderate Cellulase Loadings on Initial Glucose and Xylose Release from Corn Stover Solids Pretreated by Leading Technologies", Biotechnology and Bioengineering 102(2) (2009): p. 457-467.

Larsen, J. et al., "The IBUS Process—Lignocellulosic Bioethanol Close to a Commercial Reality", Chem. Eng. Technol. 31(5) (2008): p. 765-772.

Lynd, L.R. et al. "Consolidated bioprocessing of cellulosic biomass: an update", Current Opinion in Biotechnology 16 (2005): p. 577-583.

Mosier, N. et al., "Features of promising technologies for pretreatment of lignocellulosic biomass", Bioresource Technology 96 (2005): p. 673-686.

McMillan, J.D. "Processes for Pretreating Lignocellulosic Biomass: A Review", National Renewable Energy Laboratory (1992): Covers with Introduction; p. 1-44.

Nandini, C. et al. "Carbohydrate composition of wheat, wheat bran, sorghum and bajra with good chapatti/roti (Indian flat bread) making quality", Food Chemistry 73 (2001): p. 197-203.

Sanchez, O.J. et al., "Trends in biotechnological production of fuel ethanol from different feedstocks", Bioresource Technology 99 (2008): p. 5270-5295.

Saska, M. et al., "Aqueous Extraction of Sugarcane Bagasse Hemicellulose and Production of Xylose Syrup", Biotechnology and Bioengineering 45 (1995): p. 517-523.

Sepulveda-Huerta, E. et al. "Production of detoxified sorghum straw hydrolysates for fermentative purposes", Journal of the Science of Food and Agriculture 86 (2006): p. 2579-2586.

Spindler, D. et al., "Evaluation of Pretreated Woody Crops for the Simultaneous Saccharification and Fermentation Process", Ethanol from Biomass. FY 1988, Annual Report (1989): p. B33-B43.

Taherzadeh, M.J. et al., "Acid-based Hydrolysis Processes for Ethanol from Lignocellulosic Materials: A Review", BioResources 2(3) (2007): p. 472-499.

Taherzadeh, M.J. et al., "Enzyme-based Hydrolysis Processes for Ethanol from Lignocellulosic Materials: A Review", BioResources 2(4) (2007): p. 707-738.

Texeira, R.H. et al., "Ethanol Annual Report FY 1990", (1991): p. 1-346.

Torget, R. et al., "Dilute Acid Pretreatment of Short Rotation Woody and Herbaceous Crops", Applied Biochemistry and Biotechnology 24/25 (1990): p. 115-126.

Torget, R. et al., "Initial Design of a Dilute Sulfuric Acid Pretreatment Process for Aspen Wood Chips", Solar Energy Research Institute (1988): p. 89-104.

Torget, R. et al., "Dilute Acid Pretreatment of Corn Cobs, Corn Stover, and Short-Rotation Crops", FY 1990 Ethanol Annual Report (1991): p. 71-82.

Weil, J. et al., "Pretreatment of Corn Fiber by Pressure Cooking in Water", Applied Biochemistry and Biotechnology 73 (1998): p. 1-17.

Wyman, Charles E., "What is (and is not) vital to advancing cellulosic ethanol", Trends in Biotechnology 25(4) (2007): p. 153-157.

Wyman, C.E. et al., "Coordinated development of leading biomass pretreatment technologies", Bioresource Technology 96 (2005): p. 1959-1966.

Yang, B. et al., "Pretreatment: the key to unlocking low-cost cellulosic ethanol", Biofuels, Bioprod. Bioref. 2 (2008): p. 26-40.

Zhang, Y-H.P. et al., "Outlook for cellulose improvement: Screening and selection strategies", Biotechnology Advances 24 (2006): p. 452-481.

Zhang, Y.P. et al., "Toward an Aggregated Understanding of Enzymatic Hydrolysis of Cellulose: Noncomplexed Cellulase Systems", Biotechnology and Bioengineering 88(7) (2004): p. 797-824.

U.S. Appl. No. 12/716,989, filed Mar. 2010, Kwiatkowski.
U.S. Appl. No. 12/827,948, filed Jun. 2010, Bootsma et al.
U.S. Appl. No. 13/209,170, filed Aug. 2011, Bly et al.
U.S. Appl. No. 14/459,977, filed Aug. 2014, Bootsma.
U.S. Appl. No. 14/465,177, filed Aug. 2014, Narendranath et al.

Blank, S.L. et al. "Combustion Properties of Lignin Residue From Lignocellulose Fermentation", National Renewable Energy Laboratory, 2000, pp. 1-15.

Bura, R. et al., "Influence of Xylan on the Enzymatic Hydrolysis of Steam-Pretreated Corn Stover and Hybrid Poplar", Biotechnol. Prog. 25(2) (2009): p. 315-322.

Cara, C. et al., "Influence of solid loading on enzymatic hydrolysis of steam exploded or liquid hot water pretreated olive tree biomass", Process Biochemistry 42 (2007): p. 1003-1009.

Gao, D. et al., "Strategy for Identification of Novel Fungal and Bacterial Glycosyl Hydrolase Hybrid Mixtures that can Efficiently Saccharify Pretreated Lignocellulosic Biomass", Bioenerg. Res. 3 (2010): p. 67-81.

Guo, G.L. et al., "Characterization of enzymatic saccharification for acid-pretreated lignocellulosic materials with different lignin composition", Enzyme and Microbial Technology 45 (2009): p. 80-87.

Haagensen, F. et al. "Enzymatic Hydrolysis and Glucose Fermentation of Wet Oxidized Sugarcane Bagasse and Rice Straw for Bioethanol Production", RisØ-R-1517(EN), 2002, pp. 184-195.

Kumar, S. et al., "Recent Advances in Production of Bioethanol from Lignocellulosic Biomass", Chem. Eng. Technol. 32(4) (2009): p. 517-526.

Li, X.L. et al., "Two cellulases, CelA and CelC, from the polycentric anaerobic fungus Orpinomyces strain PC-2 contain N-terminal docking domains for a cellulosehemicellulase complex", Applied and Environmental Microbiology 63(12) (1997): p. 4721-4728.

Marchal, R. et al. "Large-Scale Enzymatic Hydrolysis of Agricultural Lignocellulosic Biomass. Part 2: Conversion Into Acetone-Butanol", Bioresource Technology 42, 1992, pp. 205-217.

Olsson, L. et al., "Fermentation of lignocellulosic hydrolysates or ethanol production", Enzyme Microb. Technol., 18 (1996): p. 312-331.

Reith, J.H. et al. "Co-Production of Bio-Ethanol, Electricity and Heat From Biomass Residues", Contribution to the $12^{th}$ European Conference and Technology Exhibition on Biomass for Energy, Industry and Climate Protection, Jun. 17-21, 2002, Amsterdam, the Netherlands, pp. 1-22.

Sun, Y. et al. "Hyrdolysis of Lignocellulosic Materials for Ethanol Production: A Review", Bioresource Technology 83, 2002, pp. 1-11.

Thomsen, M.H. et al., "Preliminary Results on Optimization of Pilot Scale Pretreatment of Wheat Straw Used in Coproduction of Bioethanol and Electricity", Applied Biochemistry and Biotechnology, vol. 129-132, 2006, p. 448.

Varga, E., et al., "High Solid Simultaneous Saccharification and Fermentation of Wet Oxidized Corn Stover to Ethanol", Biotechnol. Bioeng. 88(5), 2004, Abstract.

Xiao, Z. et al., "Effects of Sugar Inhibition on Cellulases and β-Glucosidase During Enzymatic Hydrolysis of Softwood Substrates", Applied Biochemistry and Biotechnology 113-116 (2004): p. 1115-1126.

* cited by examiner

OPERATING CONDITION

Solids (%) (in slurry provided to hydrolysis system)

OPERATING CONDITION pH

| Amt. of CTS to add (mL) | AnMBR Effluent to add (mL) | Amt. of CTS to add (frac) | AnMBR Effluent to add (frac) | Ferm ID # | Glucose % w/v | % Theoretical glucose |
|---|---|---|---|---|---|---|
| 0.0 | 0.0 | 0 | 0 | NN-S4847 | 8.03 | 71.35 |
| 0.0 | 6.3 | 0 | 0.1 | NN-S4848 | 8.88 | 77.09 |
| 0.0 | 12.6 | 0 | 0.2 | NN-S4849 | 8.75 | 77.73 |
| 0.0 | 18.8 | 0 | 0.3 | NN-S4850 | 8.88 | 78.90 |
| 6.3 | 0.0 | 0.1 | 0 | NN-S4851 | 8.71 | 77.39 |
| 6.3 | 6.3 | 0.1 | 0.1 | NN-S4852 | 9.03 | 80.21 |
| 6.3 | 12.6 | 0.1 | 0.2 | NN-S4853 | 8.86 | 78.66 |
| 6.3 | 18.8 | 0.1 | 0.3 | NN-S4854 | 8.83 | 78.43 |
| 15.7 | 0.0 | 0.25 | 0 | NN-S4855 | 8.86 | 78.68 |
| 15.7 | 6.3 | 0.25 | 0.1 | NN-S4856 | 8.89 | 78.94 |
| 15.7 | 12.6 | 0.25 | 0.2 | NN-S4857 | 8.84 | 78.51 |
| 15.7 | 18.8 | 0.25 | 0.3 | NN-S4858 | 8.71 | 77.36 |

FIG. 13

FIG. 14A
Biomass Composition

| Cob (percent) | Husks/ Leaves (percent) | Stalk (percent) | Cellulose (Glucan) (percent) | Hemicellulose | | | | Lignin (percent) | Ash (percent) |
|---|---|---|---|---|---|---|---|---|---|
| | | | | Xylan (percent) | Arabinan (percent) | Acetate (percent) | Composite (percent) | | |
| 100 | 0 | 0 | 36.0 | 33.3 | 3.6 | 3.0 | 39.9 | 14.9 | 2.2 |
| 0 | 100 | 0 | 37.2 | 25.6 | 4.9 | 2.2 | 32.7 | 13.0 | 7.7 |
| 0 | 0 | 100 | 41.7 | 22.5 | 2.4 | 2.6 | 27.5 | 18.3 | 3.7 |
| 50 | 0 | 50 | 39.8 | 27.9 | 3.0 | 2.8 | 33.7 | 16.6 | 3.0 |
| 50 | 50 | 0 | 36.6 | 29.5 | 4.2 | 2.6 | 36.3 | 14.0 | 5.0 |
| 35 | 45 | 20 | 37.7 | 27.7 | 3.9 | 2.6 | 34.2 | 14.7 | 5.0 |

FIG. 14B
Biomass

| | Cellulose (Glucan) (percent) (approx.) | Hemicellulose (percent) (approx.) | Lignin (percent) (approx.) | Ash (percent) (approx.) |
|---|---|---|---|---|
| Typical Range | 35-45 | 24-42 | 12-20 | 2-8 |
| Expected Range | 30-55 | 20-50 | 10-25 | 1-10 |

FIG. 15A
Pre-Treated Biomass Liquid Component Composition

| Cob (percent) | Husks/ Leaves (percent) | Stalk (percent) | Glucose (percent) | Xylose (percent) | Arabinose (percent) | Acetic Acid (ppm) |
|---|---|---|---|---|---|---|
| 100 | 0 | 0 | 0.4 | 4.8 | 0.5 | 6090 |
| 0 | 100 | 0 | 0.4 | 2.7 | 0.5 | 3400 |
| 0 | 0 | 100 | 0.4 | 4.2 | 0.4 | 6180 |
| 50 | 0 | 50 | 0.4 | 4.5 | 0.4 | 6135 |
| 35 | 45 | 20 | 0.4 | 3.7 | 0.5 | 4898 |

FIG. 15B
Pre-Treated Biomass
Liquid Component

|  | Glucose (percent) (approx.) | Xylose (percent) (approx.) | Arabinose (percent) (approx.) | Acetic Acid (ppm) (approx.) |
|---|---|---|---|---|
| Typical Range | 0-1 | 2-6 | 0-1 | 3000-6400 |
| Expected Range | 0-1 | 1-8 | 0-1 | 2000-8000 |

FIG. 16A
Pre-Treated Biomass
Solids Component Composition

| Cob (percent) | Husks/ Leaves (percent) | Stalk (percent) | Cellulose (Glucan) (percent) | Hemicellulose ||||  Lignin (percent) | Ash (percent) |
|---|---|---|---|---|---|---|---|---|---|
|  |  |  |  | Xylan (percent) | Arabinan (percent) | Acetate (percent) | Composite (percent) |  |  |
| 100 | 0 | 0 | 60.2 | 9.5 | 0.9 | 0.3 | 10.7 | 26.7 | 1.2 |
| 0 | 100 | 0 | 54.4 | 1.3 | 0.7 | 0.7 | 10.4 | 23.8 | 9.7 |
| 0 | 0 | 100 | 51.1 | 1.4 | 1.0 | 1.0 | 15.4 | 27.3 | 8.1 |
| 50 | 0 | 50 | 55.7 | 5.5 | 0.9 | 0.6 | 13.1 | 27.0 | 2.2 |
| 50 | 50 | 0 | 57.3 | 5.4 | 0.8 | 0.5 | 10.6 | 25.2 | 5.4 |
| 35 | 45 | 20 | 55.8 | 4.2 | 0.8 | 0.6 | 11.5 | 25.4 | 5.8 |

FIG. 16B
Pre-Treated Biomass
Solids Component

|  | Cellulose (Glucan) (percent) (approx.) | Hemicellulose (percent) (approx.) | Lignin (percent) (approx.) | Ash (percent) (approx.) |
|---|---|---|---|---|
| Typical Range | 48-62 | 8-17 | 22-30 | 1-10 |
| Expected Range | 45-65 | 6-20 | 20-32 | 1-10 |

SYSTEMS AND METHODS FOR HYDROLYSIS OF BIOMASS

CROSS-REFERENCE TO RELATED APPLICATIONS

This application claims the benefit of U.S. Provisional Application Ser. No. 61/433,864, filed Jan. 18, 2011, and entitled "SYSTEMS AND METHODS FOR HYDROLYSIS OF BIOMASS", the disclosure of which is incorporated herein by reference. This application incorporates by reference the following applications: U.S. patent Ser. No. 12/716,984 entitled "SYSTEM FOR PRE-TREATMENT OF BIOMASS FOR THE PRODUCTION OF ETHANOL", and U.S. Patent Ser. No. 61/345,486 entitled "SYSTEM FOR HYDROLYSIS OF BIOMASS TO FACILITATE THE PRODUCTION OF ETHANOL" filed May 17, 2010.

FIELD

The subject disclosure relates to treatment of biomass in the production of ethanol. The subject disclosure also relates to treatment of pre-treated biomass before the pre-treated biomass is supplied to a fermentation system in order to facilitate the efficient production of ethanol.

BACKGROUND

Ethanol can be produced from grain-based feedstocks (e.g. corn, sorghum/milo, barley, wheat, soybeans, etc.), from sugar (e.g. from sugar cane, sugar beets, etc.), and from biomass (e.g. from cellulosic feedstocks such as switchgrass, corn cobs and stover, wood or other plant material).

Biomass comprises plant matter that can be suitable for direct use as a fuel/energy source or as a feedstock for processing into another bioproduct (e.g., a biofuel such as cellulosic ethanol) produced at a biorefinery (such as an ethanol plant). Biomass may comprise, for example, corn cobs and stover (e.g., stalks and leaves) made available during or after harvesting of the corn kernels, fiber from the corn kernel, switchgrass, farm or agricultural residue, wood chips or other wood waste, and other plant matter. In order to be used or processed, biomass will be harvested and collected from the field and transported to the location where it is to be used or processed.

In a biorefinery configured to produce ethanol from biomass, such as cellulosic feedstocks as indicated above, ethanol is produced from lignocellulosic material (e.g. cellulose and/or hemi-cellulose). The biomass is prepared so that sugars in the cellulosic material (such as glucose from the cellulose and xylose from the hemi-cellulose) can be accessed and fermented into a fermentation product that comprises ethanol (among other things). The fermentation product is then sent to the distillation system, where the ethanol is recovered by distillation and dehydration. Other bioproducts such as lignin and organic acids may also be recovered as co-products. Determination of how to more efficiently prepare and treat the biomass for production into ethanol will depend upon (among other things) the form and type or composition of the biomass.

One of the costly steps in the preparation of lignocellulosic material for fermentation is the hydrolysis of the cellulosic material, which requires the usage of enzymes in order to degrade the cellulose to sugars. Typically, large doses of enzymes are required for hydrolysis since it is believed that lignin may bind to some of the enzymes rendering them inactive. As enzymes are a significant portion of the overall cost of hydrolysis, there is an inefficiency in conventional techniques that has not been addressed.

SUMMARY

An aspect relates to a method for treating lignocellulosic biomass to be supplied to a fermentation system for production of a fermentation product. The method comprises pre-treating the biomass into pre-treated biomass and separating the pre-treated biomass into a liquid component comprising sugars and a solids component comprising cellulose and lignin. The method also comprises treating the solids component of the pre-treated biomass into a treated component. The biomass comprises lignocellulosic material. Treating the solids component comprises application of an enzyme formulation and an agent to form a slurry. The enzyme formulation comprises a cellulase enzyme. The agent may include clarified thin stillage or effluent from an anaerobic membrane digester, in some embodiments.

According to an embodiment, treating the solids component releases sugar. According to another embodiment, pre-treating the biomass comprises steeping, wherein the steeping comprises mixing the biomass and applying sulfuric acid to the biomass.

DESCRIPTION OF THE DRAWINGS

In order that the disclosed aspects may be more clearly ascertained, some embodiments will now be described, by way of example, with reference to the accompanying drawings, in which:

FIG. 13 is a table of the results of biomass hydrolysis with varying concentrations of anaerobic membrane bioreactor effluent additive agent and clarified thin stillage additive agent, according to an exemplary embodiment.

FIGS. 14A and 14B list the composition of biomass comprising lignocellulosic plant material from the corn plant according to exemplary and representative embodiments.

FIGS. 15A and 15B list the composition of the liquid component of pre-treated biomass according to exemplary and representative embodiments.

FIGS. 16A and 16B list the composition of the solids component of pre-treated biomass according to exemplary and representative embodiments.

DESCRIPTION OF THE EMBODIMENTS

The various aspects will now be described in detail with reference to several embodiments thereof as illustrated in the accompanying drawings. In the following description, numerous specific details are set forth in order to provide a thorough understanding of embodiments of the one or more aspects. It will be apparent, however, to one skilled in the art, that embodiments may be practiced without some or all of these specific details. In other instances, well known process steps and/or structures have not been described in detail in order to not unnecessarily obscure the various aspects. The features and advantages of embodiments may be better understood with reference to the drawings and discussions that follow.

Aspects relate to systems and methods for enzyme hydrolysis of the solid portion of lignocellulosic hydrolysate using the addition of an agent in order to reduce enzyme load requirements and increase efficiency. Various aspects disclosed herein provide for treating biomass in the production of ethanol. Aspects also provide for improving efficiencies of the hydrolysis of cellulose. The systems and methods of the aspects disclosed herein provide cost effective means for increasing the efficiency of the conversion of cellulosic materials into fermentable sugars.

Figure 1A:
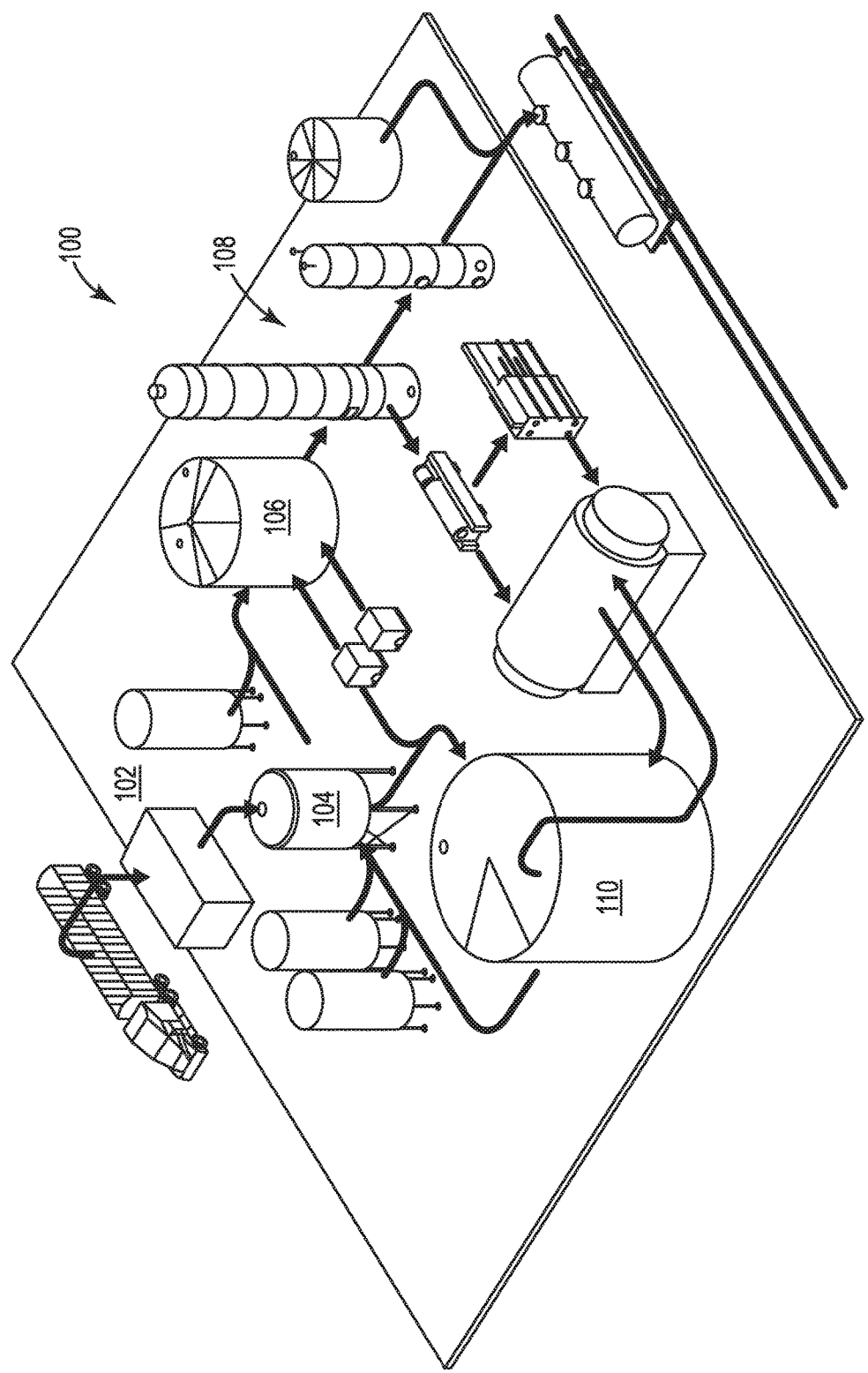
FIG. 1A is a perspective view of a biorefinery comprising an ethanol production facility, in accordance with some embodiments.

Referring to FIG. 1A, an example biorefinery 100 comprising an ethanol production facility configured to produce ethanol from biomass is shown. The example biorefinery 100 comprises an area where biomass is delivered and prepared to be supplied to the ethanol production facility. The cellulosic ethanol production facility comprises apparatus for preparation 102, pre-treatment 104 and treatment of the biomass into treated biomass suitable for fermentation into fermentation product in a fermentation system 106. The cellulosic ethanol production facility comprises a distillation system 108 in which the fermentation product is distilled and dehydrated into ethanol. As shown in FIG. 1A, a waste treatment system 110 (shown as comprising an anaerobic digester and a generator) can be included in the biorefinery 100. According to other alternative embodiments, the waste treatment system may comprise other equipment configured to treat, process, and recover components from the cellulosic ethanol production process, such as a solid/waste fuel boiler, anaerobic digester, aerobic digester or other biochemical or chemical reactors.

Figure 1B:
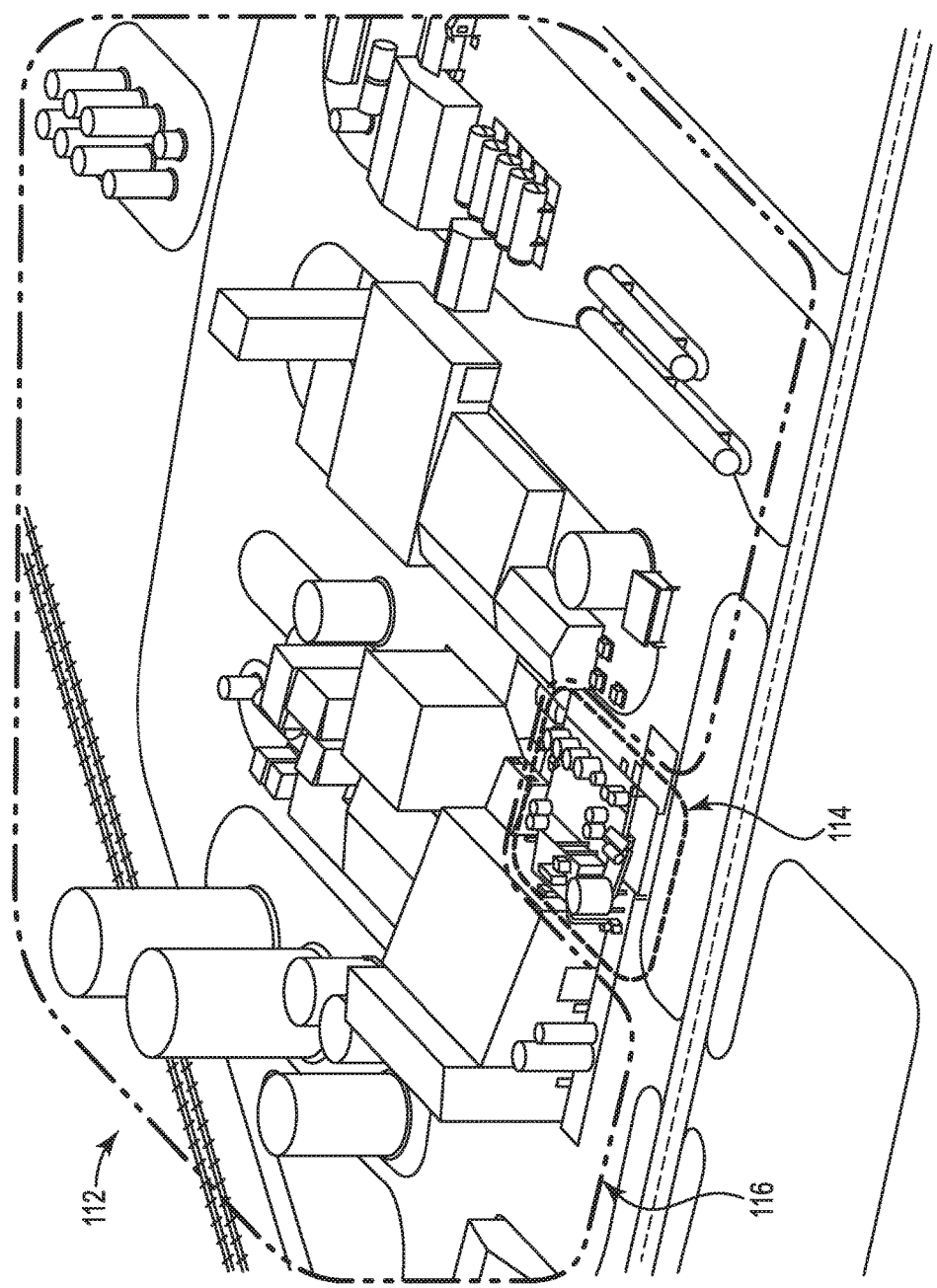
FIG. 1B is another perspective view of a biorefinery comprising an ethanol production facility, in accordance with some embodiments.

As shown in FIG. 1B, according to an exemplary embodiment, a biorefinery 112 may comprise a cellulosic ethanol production facility 114 (which produces ethanol from lignocellulosic material and components of the corn plant) co-located with a corn-based ethanol production facility 116 (which produces ethanol from starch contained in the endosperm component of the corn kernel). As indicated in FIG. 1B, by co-locating the two ethanol production facilities, certain plant systems may be shared, for example, systems for dehydration, storage, denaturing and transportation of ethanol, energy/fuel-to-energy generation systems, plant management and control systems, and other systems. Corn fiber (a component of the corn kernel), which can be made available when the corn kernel is prepared for milling (e.g. by fractionation) in the corn-based ethanol production facility, may be supplied to the cellulosic ethanol production facility as a feedstock. Fuel or energy sources such as methane or lignin from the cellulosic ethanol production facility may be used to supply power to either or both co-located facilities. According to other alternative embodiments, a biorefinery (e.g. a cellulosic ethanol production facility) may be co-located with other types of plants and facilities, for example an electric power plant, a waste treatment facility, a lumber mill, a paper plant, or a facility that processes agricultural products.

Figure 2:
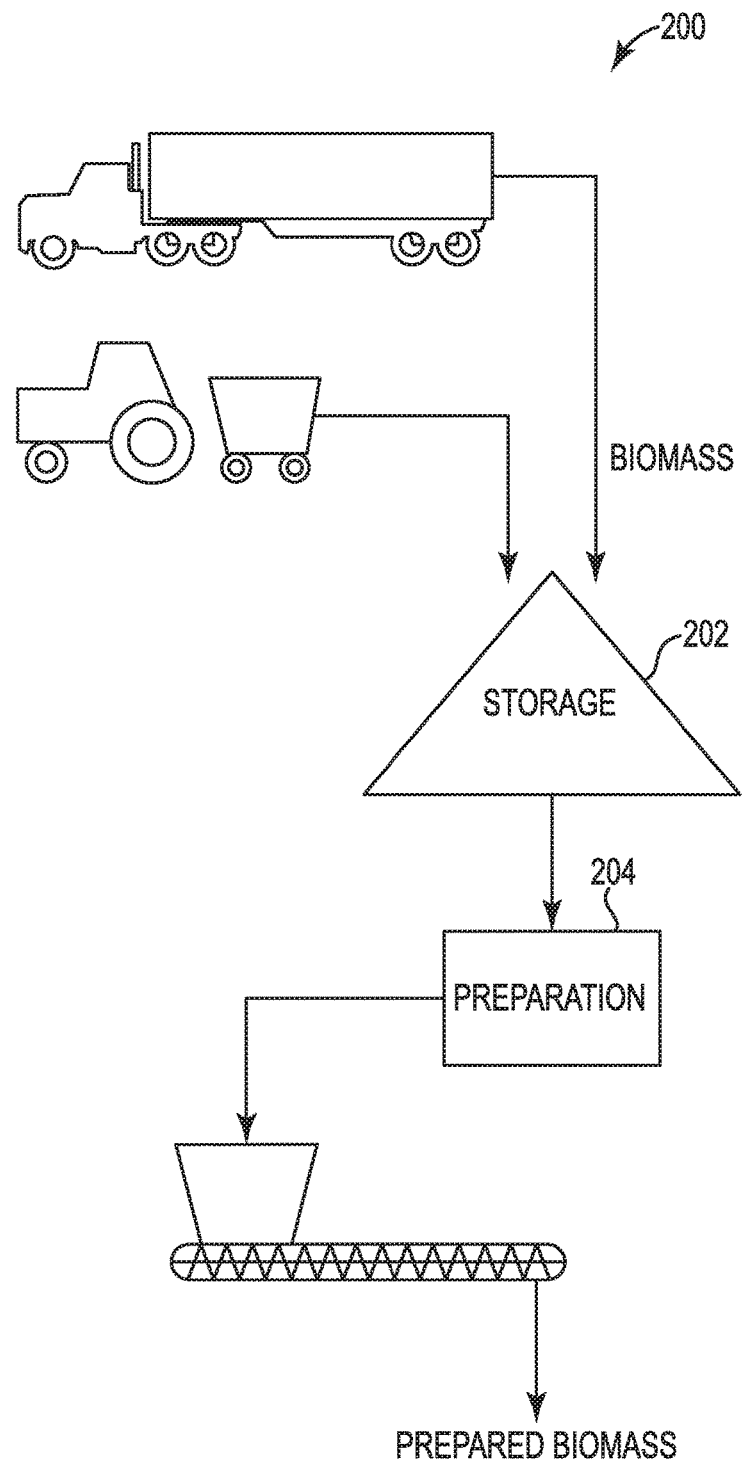
FIG. 2 is a system for the preparation of biomass delivered to a biorefinery, in accordance with some embodiments.

Referring to FIG. 2, a system 200 for preparation of biomass delivered to the biorefinery is shown. The biomass preparation system may comprise an apparatus for receipt/unloading of the biomass, cleaning (e.g. removal of foreign matter), grinding (e.g. milling, reduction or densification), and transport and conveyance for processing at the plant. According to an exemplary embodiment, biomass in the form of corn cobs and stover may be delivered to the biorefinery and stored 202 (e.g. in bales, piles or bins, etc.) and managed for use at the facility. According to an exemplary embodiment, the biomass may comprise at least about 20 to 30 percent corn cobs (by weight) with corn stover and other matter. According to other exemplary embodiments, the preparation system 204 of the biorefinery may be configured to prepare any of a wide variety of types of biomass (e.g. plant material) for treatment and processing into ethanol and other bioproducts at the plant.

Figure 3A:
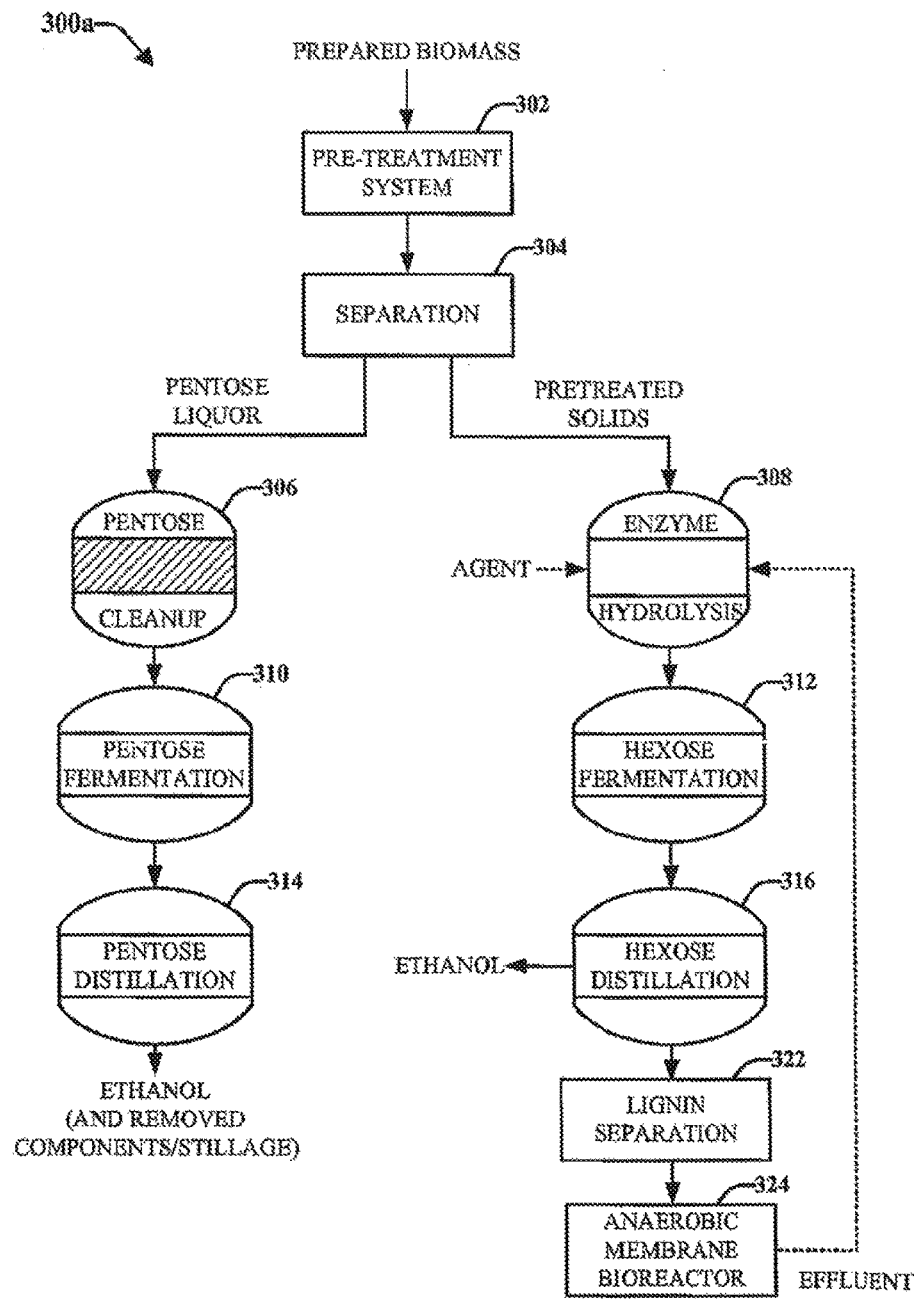
FIGS. 3A and 3B are alternate embodiments of a schematic diagram of the cellulosic ethanol production facility, in accordance with some embodiments.
Figure 3B:
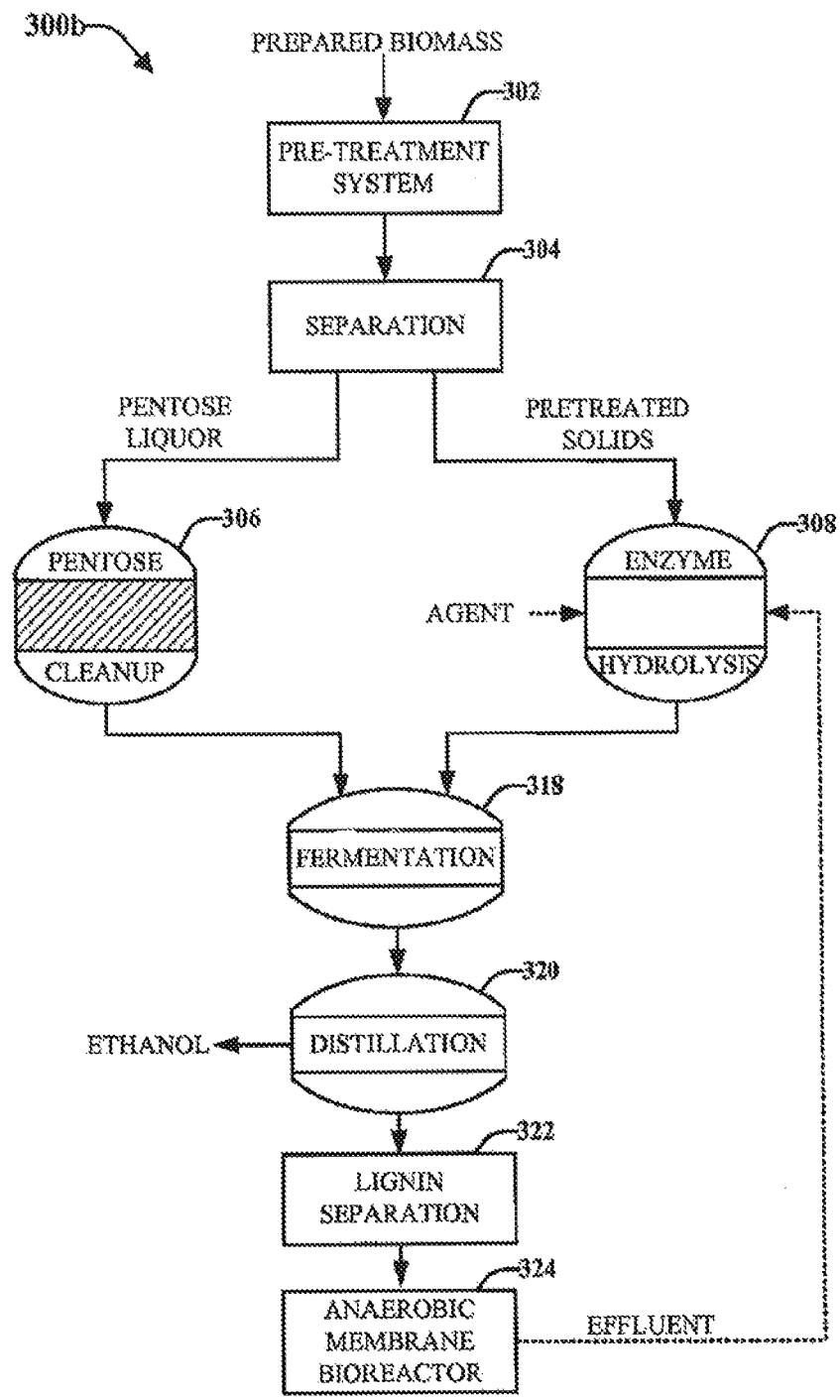

Referring to FIGS. 3A and 3B, alternate embodiments of a schematic diagram of the cellulosic ethanol production facility 300a and 300b are shown. According to some embodiments, biomass comprising plant material from the corn plant is prepared and cleaned at a preparation system. After preparation, the biomass is mixed with water into a slurry and is pre-treated at a pre-treatment system 302. In the pre-treatment system 302, the biomass is broken down (e.g. by hydrolysis) to facilitate separation 304 into a liquid component (e.g. a stream comprising the C5 sugars, known as pentose liquor) and a solids component (e.g. a stream comprising cellulose from which the C6 sugars can be made available). The C5-sugar-containing liquid component (C5 stream or pentose liquor) may be treated in a pentose cleanup treatment system 306. In a similar manner, the C6-sugar-containing pretreated solids component may be treated in a solids treatment system using enzyme hydrolysis 308 to generate sugars. According to an embodiment, hydrolysis (such as enzyme hydrolysis) may be performed to access the C6 sugars in the cellulose; treatment may also be performed in an effort to remove lignin and other non-fermentable components in the C6 stream (or to remove components such as residual acid or acids that may be inhibitory to efficient fermentation). Enzyme hydrolysis efficiency may be increased through the addition of an agent.

Such agents may include anaerobic membrane digester effluent, clarified thin stillage, wet cake, whole stillage, other viable protein source, or combinations thereof. Details of the treatment of the C6 solids will be described in detail below.

In accordance with the embodiments of FIG. 3A, the treated pentose liquor may then be fermented in a pentose fermentation system 310, and the fermentation product may be supplied to a pentose distillation system 314 for ethanol recovery. In a similar manner, the treated solids, not including substantial amounts of C6 sugars, may be supplied to a hexose fermentation system 312, and the fermentation product may be supplied to a hexose distillation system 316 for ethanol recovery. The stillage from the distillation may then be treated at a lignin separation system 322 to generate a liquid component and a solid wet cake. The wet cake may then be supplied to an Anaerobic Membrane Bioreactor (AnMBR) 324 for further treatment. In some embodiments, effluent from the anaerobic membrane bioreactor 324 may be recycled to the enzyme hydrolysis 308 tank as an additive agent.

In the alternate embodiment of FIG. 3B, the resulting treated pentose liquor and treated solids may be combined after treatment (e.g. as a slurry) for co-fermentation in a fermentation system 318. Fermentation product from the fermentation system 318 is supplied to a combined distillation system 320 where the ethanol is recovered. According to any embodiment, a suitable fermenting organism (ethanologen) can be used in the fermentation system. In accordance with some aspects, the selection of an ethanologen may be based on various considerations, such as the predominant types of sugars present in the slurry. Dehydration and/or denaturing of the ethanol produced from the C5 stream and the C6 stream may be performed either separately or in combination. As with the previously described embodiments, the stillage from the distillation may be treated at a lignin separation system 322 to generate a liquid component and a solid wet cake. The wet cake may be supplied to an Anaerobic Membrane Bioreactor (AnMBR) 324 for further treatment. In some embodiments, effluent from the anaerobic membrane bioreactor 324 may be recycled to the enzyme hydrolysis 308 tank as an additive agent.

During treatment of the C5 and/or C6 stream, components may be processed to recover byproducts, such as organic acids and lignin. The removed components during treatment and production of ethanol from the biomass from either or both the C5 stream and the C6 stream (or at distillation) can be treated or processed into bioproducts or into fuel (such as lignin for a solid fuel boiler or methane produced by treatment of residual/removed matter such as acids and lignin in an anaerobic digester) or recovered for use or reuse.

According to an embodiment, the biomass comprises plant material from the corn plant, such as corn cobs, corn plant husks and corn plant leaves and corn stalks (e.g. at least the upper half or three-quarters portion of the stalk). According to some aspects, the composition of the plant material (e.g. cellulose, hemicellulose and lignin) will be approximately as indicated in FIGS. 14A and 14B (e.g. after at least initial preparation of the biomass, including removal of any foreign matter). According to an embodiment, the plant material comprises corn cobs, husks/leaves and stalks . . . . For example, the plant material may comprise (by weight) up to 100 percent cobs, up to 100 percent husks/leaves, approximately 50 percent cobs and approximately 50 percent husks/leaves, approximately 30 percent cobs and approximately 50 percent husks/leaves and approximately 20 percent stalks, or any of a wide variety of other combinations of cobs, husks/leaves and stalks from the corn plant. See FIG. 14A. According to an alternative embodiment, the lignocellulosic plant material may comprise fiber from the corn kernel (e.g. in some combination with other plant material). FIG. 14B provides various ranges believed to be representative of the composition of biomass comprising lignocellulosic material from the corn plant. According to exemplary embodiments, the lignocellulosic plant material of the biomass (from the corn plant) can comprise (by weight) cellulose at about 30 to 55 percent, hemicellulose at about 20 to 50 percent, and lignin at about 10 to 25 percent. According to another exemplary embodiment, the lignocellulosic plant material of the biomass (e.g. cobs, husks/leaves and stalk portions from the corn plant) can comprise (by weight) cellulose at about 35 to 45 percent, hemicellulose at about 24 to 42 percent, and lignin at about 12 to 20 percent. According to a particular embodiment, pre-treatment of the biomass can yield a liquid component that comprises (by weight) xylose at no less than about 1.0 percent and a solids component that comprises (by weight) cellulose (from which glucose can be made available) at no less than about 45 percent.

Figure 4A:
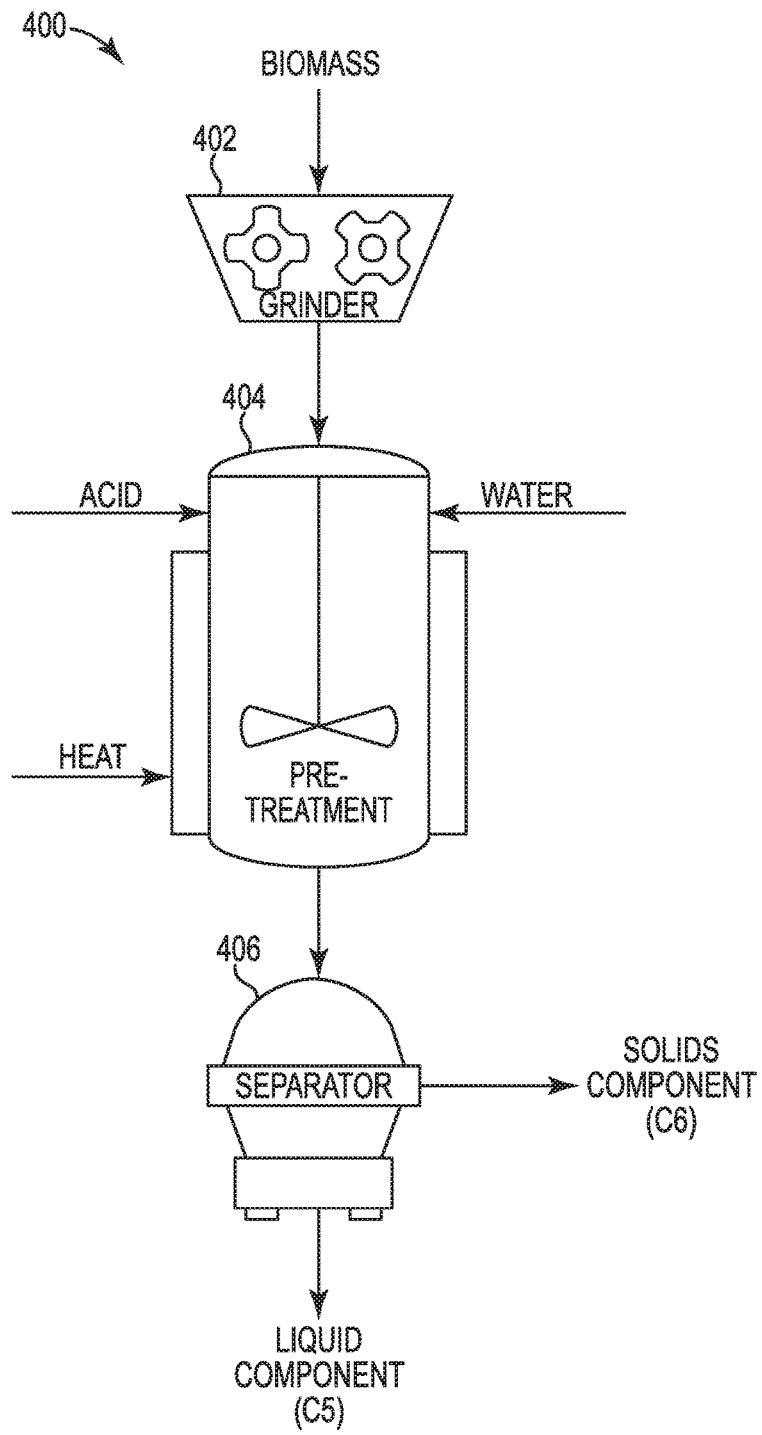
FIG. 4A is a process flow diagram illustrating the pre-treatment process, in accordance with some embodiments.
Figure 4B:
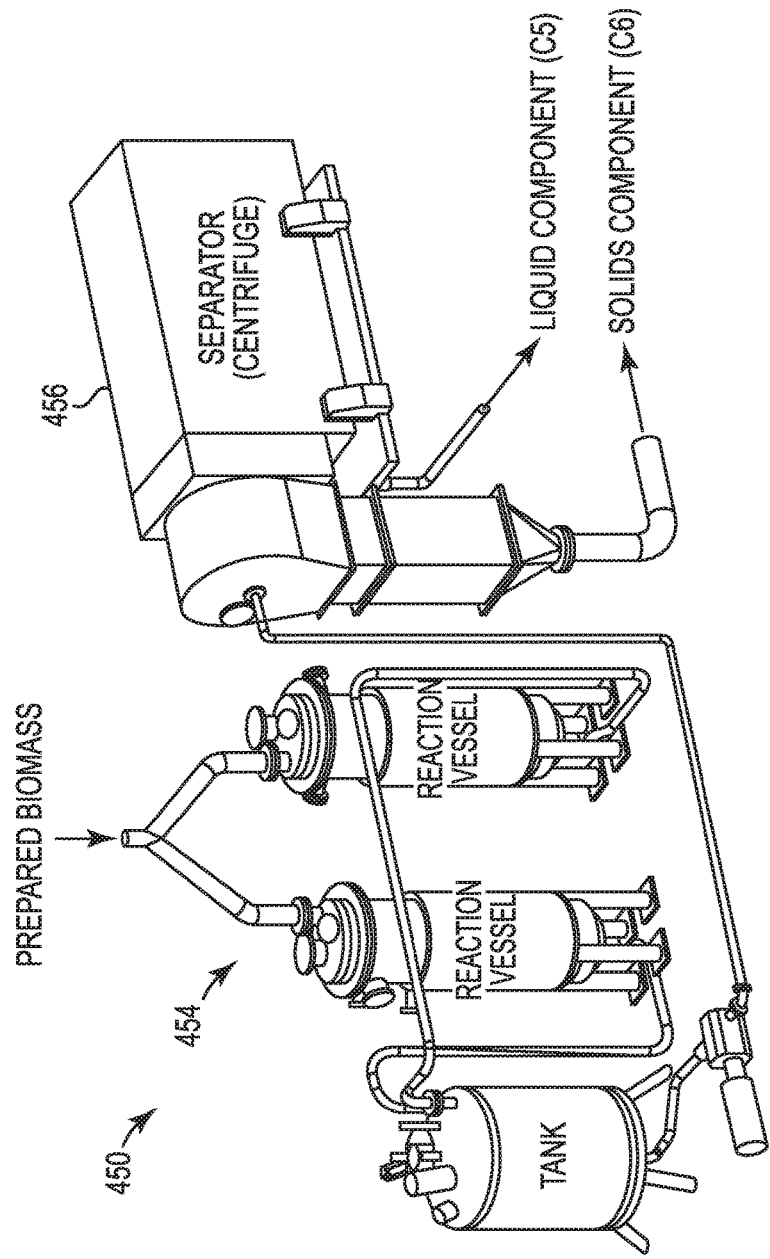
FIG. 4B is a schematic perspective view of the pretreatment process, in accordance with some embodiments.

FIGS. 4A and 4B show apparatuses 400, 450 that can be used for preparation, pre-treatment and separation of lignocellulosic biomass according to an exemplary embodiment. As shown, biomass is prepared in a grinder 402 (e.g. a grinder or other suitable apparatus or mill). Pre-treatment of the prepared biomass is performed in a reaction vessel 404 (or set of reaction vessels 454) supplied with prepared biomass and acid/water in a predetermined concentration (or pH) and other operating conditions. The pre-treated biomass can be separated in a separator 406. As shown in FIG. 4B, the pre-treated biomass can be separated in a centrifuge 456 into a liquid component (C5 stream comprising primarily liquids with some solids) and a solids component (C6 stream comprising liquids and solids such as lignin and cellulose from which glucose can be made available by further treatment).

According to an embodiment, pre-treatment of biomass can be performed as described in U.S. patent Ser. No. 12/716,984 entitled "SYSTEM FOR PRE-TREATMENT OF BIOMASS FOR THE PRODUCTION OF ETHANOL", which is incorporated by reference in its entirety.

According to an embodiment, in the pre-treatment system an acid can be applied to the prepared biomass to facilitate the breakdown of the biomass for separation into the liquid (pentose liquor) component (C5 stream from which fermentable C5 sugars can be recovered) and the solids component (C6 stream from which fermentable C6 sugars can be accessed). According to some embodiments, the acid can be applied to the biomass in a reaction vessel under determined operating conditions (e.g. acid concentration, pH, temperature, time, pressure, solids loading, flow rate, supply of process water or steam, etc.) and the biomass can be agitated/mixed in the reaction vessel to facilitate the breakdown of the biomass. According to exemplary embodiments, an acid such as sulfuric acid, hydrochloric acid, nitric acid, phosphoric acid, acetic acid, etc. (or a formulation/mixture of acids) can be applied to the biomass. According to a particular embodiment, sulfuric acid can be applied to the biomass in pre-treatment. According to a particular embodiment, the prepared biomass may be pretreated with approximately 0.8 to 1.5 percent acid (such as sulfuric acid) and about 12 to 25 percent biomass solids at a temperature of approximately 100 to 180 degrees Celsius for approximately 5 to 180 minutes. The pre-treatment may also comprise a steam explosion step, where biomass is heated to and held at (e.g. hold time) approximately 150 to 165 degrees Celsius under pressure (e.g. 100 psi) at a pH of about 1.4 to 1.6 for one to 15 minutes, and the pressure is released to further aid in the breakdown of cellulose. After pretreatment the pre-treated biomass is separated into a solids component (C6) and a liquid pentose liquor component (C5), as shown in FIGS. 4A and 4B.

The liquid pentose liquor component (C5 stream) comprises water, dissolved sugars (such as xylose, arabinose and glucose) to be made available for fermentation into ethanol, acids and other soluble components recovered from the hemicellulose. (FIG. 15B provides typical and expected ranges believed to be representative of the composition of biomass comprising lignocellulosic material from the corn plant.) According to an exemplary embodiment, the liquid component may comprise approximately 5 to 7 percent solids (e.g. suspended/residual solids such as partially hydrolysed hemicellulose, cellulose and lignin). According to a particular embodiment, the liquid component may comprise at least 2 to 4 percent xylose (by weight). According to other exemplary embodiments, the liquid component may comprise no less than 1 to 2 percent xylose (by weight). FIGS. 15A and 15B list the composition of the liquid component of pre-treated biomass (from prepared biomass as indicated in FIGS. 14A and 14B) according to exemplary and representative embodiments.

The solids component (C6 stream) comprises water, acids, and solids such as cellulose from which sugar, such as glucose, can be made available for fermentation into ethanol, and lignin. (FIG. 16B provides ranges that can be representative of the composition of biomass comprising lignocellulosic material from the corn plant.) According to an exemplary embodiment, the solids component may comprise approximately 10 to 40 percent solids (by weight) (after separation). According to a particular embodiment, the solids component may comprise approximately 20 to 30 percent solids (by weight). According to another embodiment, the solids in the solids component may comprise no less than 30 percent cellulose and the solids component may also comprise other dissolved sugars (e.g. glucose and xylose). FIGS. 16A and 16B list the composition of the solids component of pre-treated biomass (from prepared biomass as indicated in FIGS. 14A and 14B) according to exemplary and representative embodiments.

Figure 5:
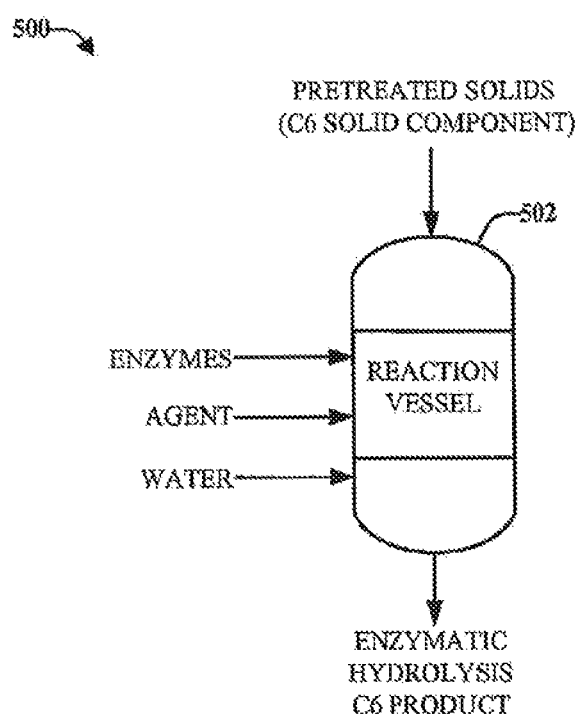
FIG. 5 is a process flow diagram illustrating the process for hydrolysis of the C6 biomass solids, in accordance with some embodiments.
Figure 6A:
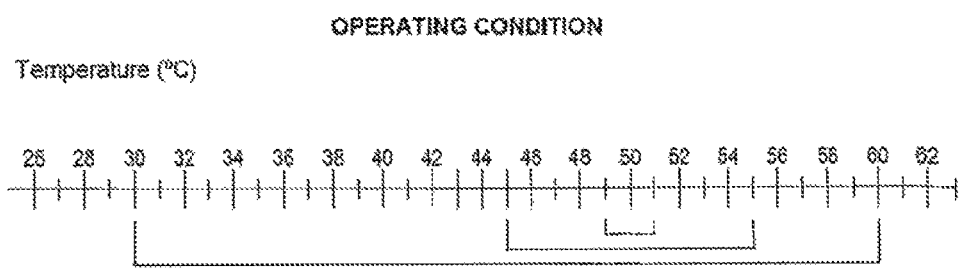
FIGS. 6A through 6D are diagrams of the operating conditions for hydrolysis of biomass according to an exemplary embodiment.
Figure 6B:
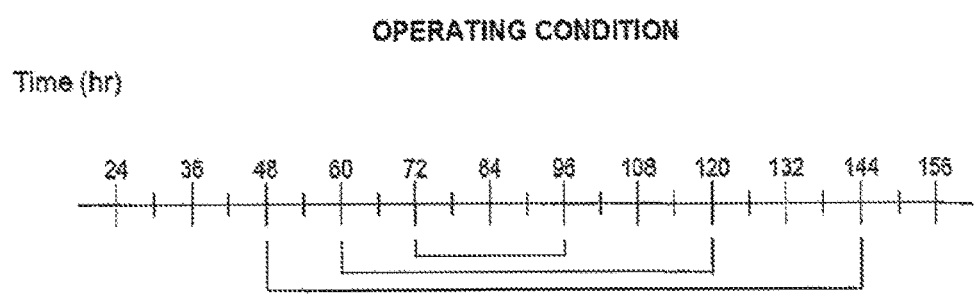
Figure 6C:
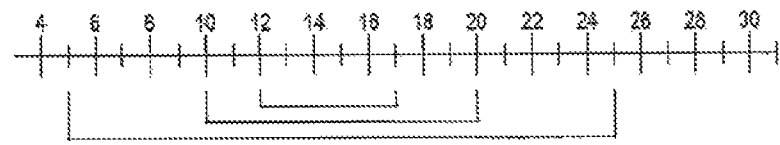
Figure 6D:
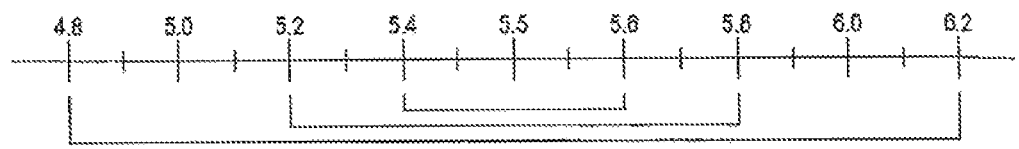

Referring to FIG. 5, after the separation of the C5 liquid component from the C6 solids, the solids may further be treated in an enzymatic hydrolysis system 500. According to an embodiment, after pre-treatment the solids component (C6) is supplied to a vessel 502 for enzymatic hydrolysis (or saccharification) along with enzymes, agents, and water. The enzymes can facilitate the breakdown of pre-treated cellulose into sugar (e.g. glucose) to generate an enzymatic hydrolysis product. The sugar rich enzymatic hydrolysis product may then be fermented into ethanol, or used for any other downstream process.

In some embodiments, the C6 solids may be subjected to a sequential hydrolysis and fermentation (SHF) process, wherein the solids are subjected to an enzyme hydrolysis (with a glucan conversion of at least 80%) followed by a fermentation. While requiring a two-step process, with the SHF approach enzyme hydrolysis may be performed at optimal pH and temperature for conversion of cellulose to sugars. Typically, for SHF, the solids are treated at about 50 degrees Celsius, pH 5.5 and 15% total solids slurry with cellulase.

Alternatively, the C6 solids may be subjected to a simultaneous saccharification and fermentation (SSF) process wherein the enzyme hydrolysis and fermentation is performed at about the same time. Simultaneous saccharification and fermentation can be performed at temperatures suitable for ethanol production by the yeast (e.g., about 37° C.) which may be less than optimal for the cellulase enzyme. As such, enzyme efficiency may be reduced. For both SSF and SHF binding of the cellulase enzymes to lignin may be a particular concern as, dependent upon the feedstock used, lignin can be dispersed on to the solids after dilute acid pretreatment, as discussed above. This may be particularly problematic when corn stover biomass is utilized as a feedstock.

According to an exemplary embodiment, an enzyme formulation comprising an enzyme capable of hydrolysing cellulose is supplied to the solids component (C6) to facilitate the enzyme hydrolysis, e.g. the saccharification by enzyme action of the polymeric cellulose (e.g. polymeric glucan) into accessible monomeric sugars (e.g. monomeric glucose). An example of such cellulase enzyme is Cellic CTec (e.g. NS22074) from Novozymes North America, Inc. of Franklinton, N.C. The amount or loading (dose) of enzyme formulation may be varied as an operating condition. According to an exemplary embodiment, approximately 2 to 12 milligrams of enzyme protein per gram of cellulose may be added. According to a particular embodiment, approximately 3 to 9 milligrams of enzyme protein per gram of cellulose may be added. In accordance with some aspects, the addition of agents to boost enzyme efficiencies is utilized for the enzymatic hydrolysis of cellulose containing materials. Given that enzymes are responsible for a large portion of the cost associated with the hydrolysis of cellulose materials, reducing the enzyme loading required, or gaining cellulose conversion efficiency, may be beneficial in the marketplace.

As such, embodiments disclosed herein are directed toward the addition of agents to the reaction vessel 502 in order to improve the efficiency and yield of enzymatic hydrolysis of pre-treated cellulose. The pretreated solids include lignin and other materials which may bind proteins. When enzymes are added to the reaction vessel 502 some portion of these enzymes become bound by the lignin and/or other particulates. This may render the bound enzymes less efficient, or even inactive. As such, enzyme efficiency of the entire hydrolysis decreases. In order to overcome this reduction in efficiency, traditionally a greater level of enzymes were added.

When the addition of another protein source is provided, by way of an agent, these proteins may compete for binding sites on the lignin material. This results in less binding of the enzymes and a correlated increase in hydrolysis efficiency. Possible sources of protein-rich byproducts in an ethanol plant include thin stillage, Anaerobic Membrane Bioreactor (AnMBR) effluent, wet cake, whole stillage and other byproducts. Particular examples of agent additives for the improvement of hydrolysis efficiency will be discussed in greater detail below.

According to a first embodiment, the agent may comprise a thin stillage composition from a conventional (e.g. corn based) ethanol production facility. According to a particular embodiment, the agent may comprise clarified thin stillage from a conventional (e.g. corn based) ethanol production facility. Clarified thin stillage can be produced from thin stillage by removal of substantially all of solids and oil contained in the thin stillage. Clarified thin stillage comprises essentially water and soluble components of thin stillage. According to an embodiment, the agent comprises as an active component at least a part of the soluble components comprised in thin stillage.

According to a second embodiment, the agent may comprise an effluent composition from the anaerobic membrane bioreactor of a cellulosic (e.g. biomass based) ethanol production facility. The lignin cake that results after distillation in the biomass based ethanol plant is digested in an anaerobic membrane bioreactor type. Digestion of the wet cake materials by anaerobic microorganisms substantially maintains nutrient value of the material. The membrane separates the relatively clean effluent from the solids and microorganisms. The effluent from the digester can have high levels of extracellular polymeric substances (EPS) that include protein, lipids, and nucleic acids.

The active protein components that are present in thin stillage and anaerobic membrane bioreactor effluent may also be present in other fermentation products or co-products and intermediates, such as beer, whole stillage, wet cake, syrup, backset and dried distillers grains (with or without solubles), any of which may be used as a constituent of the agent, according to an embodiment. According to an alternative embodiment, the agent may comprise corn germ steep liquor, which can be produced by steeping corn germ (produced for example in a fractionation system from corn kernels) in water or a water based liquid. Other agents (e.g. potassium hydroxide or sodium hydroxide for pH adjustment) may also be supplied to the treatment vessel.

The amount of thin stillage, clarified thin stillage, and/or anaerobic membrane bioreactor effluent applied to the treatment of the solids component (C6) may vary from about 1 to 90 percent of all the liquid present, according to an exemplary embodiment. According to an embodiment, the amount of thin stillage, clarified thin stillage, or anaerobic membrane bioreactor effluent may vary from about 20 to 70 percent of all the liquid present.

FIGS. 6A through 6D show operating conditions for subject parameters for the treatment of the solids component of pre-treated biomass to hydrolyse the cellulose into sugar according to an exemplary embodiment. Operating conditions are shown in the form of nested ranges comprising an acceptable operating range (the outer/wide range shown), an example operating range (the middle range shown), and a specific example operating range (the inner/narrow range shown) for each subject condition or parameter.

According to an exemplary embodiment, the temperature during the treatment of the solids component (C6) may be approximately 30 to 60 degrees Celsius. According to an embodiment, the temperature during the treatment of the solids component (C6) may be approximately 45 to 55 degrees Celsius. According to a particular embodiment, the temperature during the treatment of the solids component (C6) may be approximately 49 to 51 degrees Celsius.

According to an exemplary embodiment, the treatment time of the solids component (C6) may be approximately 48 to 144 hours. According to an embodiment, the treatment time of the solids component (C6) may be approximately 60 to 120 hours, and according to a particular embodiment, the treatment time of the solids component (C6) may be approximately 72 to 96 hours.

According to an exemplary embodiment, the solids content of the solids component (C6) supplied to the treatment system may be approximately 5 to 25 percent by weight. According to an embodiment, the solids content of the solids component (C6) may be approximately 10 to 20 percent by weight. According to a particular embodiment, the solids content of the solids component (C6) may be approximately 12 to 17 percent by weight.

According to an exemplary embodiment, the pH during the treatment of the solids component (C6) may be approximately 4.8 to 6.2. According to an embodiment, the pH during the treatment of the solids component (C6) may be approximately 5.2 to 5.8. According to a particular embodiment, the pH during the treatment of the solids component (C6) may be approximately 5.4 to 5.6.

Figure 7:
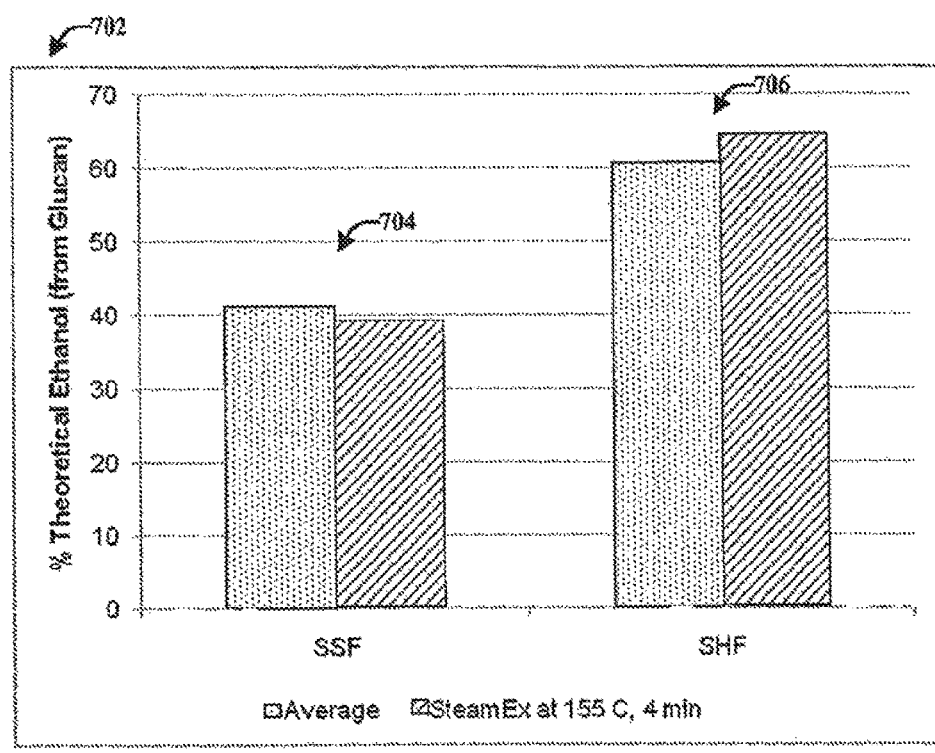
FIG. 7 is an example graph for the percent of theoretical ethanol generated from biomass under various process treatments, in accordance with some embodiments.

As illustrated in the graph of FIG. 7, a glucose yield that may be achieved during enzyme hydrolysis of biomass (e.g. corn cobs, husks, leaves and/or stalks) using available cellulase enzymes without the addition of thin stillage, clarified thin stillage, or anaerobic membrane bioreactor effluent may be in the range of about 35 to 40 percent of theoretical (e.g. calculated) glucose yield 702 for simultaneous saccharification and fermentation (SSF) 704 and between about 55 to 70 percent of theoretical glucose yield for sequential hydrolysis and fermentation (SHF) 704. Exact glucose yields may vary dependent upon pretreatment procedures. For example, as illustrated in the graph, inclusion of steam explosion pretreatment, as described above, may increase glucose conversion yields for SHF processed biomass. According to embodiments, an increase of up to 45 to 110 percent in glucose yield during enzyme hydrolysis may be achieved through the addition of a lignin-binding agent, such as clarified thin stillage and/or Anaerobic Membrane Bioreactor (AnMBR) effluent.

EXAMPLES

A series of limited examples were conducted according to an exemplary embodiment of the system in an effort to evaluate the effect of using various agents in the treatment of the solids component (C6). Experiments and tests were conducted to evaluate glucose yields for C6 hydrolysis with the addition of various agents. The following examples are intended to provide clarity to some embodiments of systems and means of operation and is not intended to limit the scope of the disclosed aspects.

The system used for the examples comprised a temperature-controlled reaction vessel and a pressure tube. Biomass comprising roughly 35 percent cob, 45 percent husks and leaves, and 20 percent stalks was pre-treated by steeping with approximately 1 to 1.3 percent acid (e.g. sulfuric acid) at 140 degrees Celsius with 14.3 percent solids for 50 minutes and by steam explosion at pH 1.5, at roughly 154 degrees Celsius and a hold time of 4 minutes. The pre-treated biomass slurry was supplied to the reaction vessels along with make-up water and enzymes to reach 12 to 15 percent solids and was studied for conversion of cellulose to glucose. Fermentation yields for the resulting hydrolysis product were also measured.

Example 1

In the first example, the pre-treated biomass was supplied to two reaction vessels with make-up water. The make-up water in one vessel consisted of water, and the make-up water in another vessel comprised 40 percent water and 60 percent clarified thin stillage. The clarified thin stillage was generated by centrifuging thin stillage (7% solids) at 5000 rpm for 20 minutes. After centrifugation, three layers are present: a solid pellet, a liquid middle layer, and an oil emulsion top layer. The middle liquid layer contains 4% solids and is considered clarified thin stillage. This layer was removed and used for the following examples.

The pH of the slurry was adjusted to 5.5 with potassium hydroxide and about 7.2 milligrams of cellulase containing enzyme formulation (e.g. Cellic CTec2, available from Novozymes North America, Inc. of Franklinton, N.C.) per gram of cellulose was added to each vessel. Enzyme hydrolysis was conducted at 50 degrees Celsius. The amount of glucose in each vessel was measured at 0, 24, 48, 72, and 96 hours by high pressure liquid chromatography (HPLC).

Figure 8:
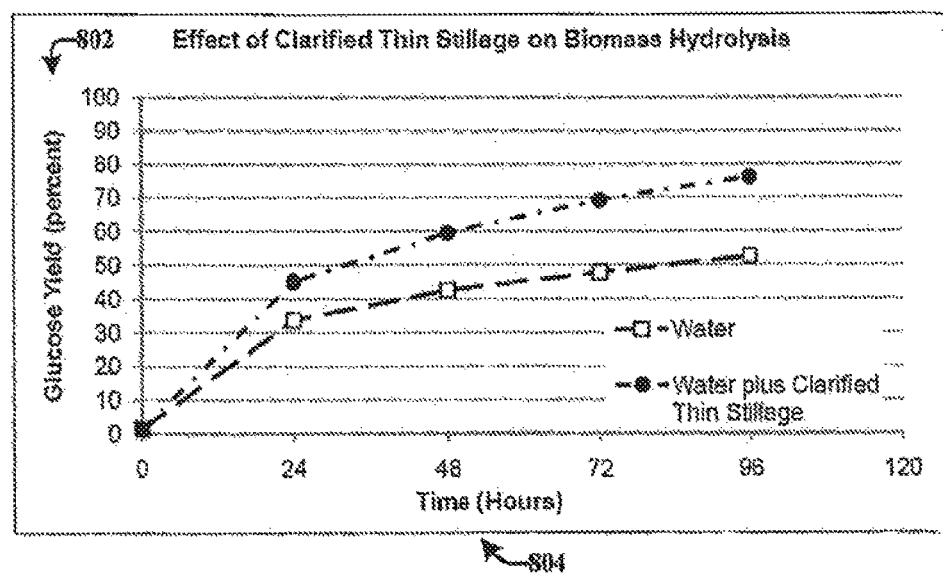
FIG. 8 is a graph of the results of biomass hydrolysis with and without a clarified thin stillage additive agent, according to an exemplary embodiment.

It was observed that at 96 hours the glucose yield of the biomass with water only was approximately 52.6 percent of theoretical, and the glucose yield of the biomass with water and clarified thin stillage was approximately 76.1 percent. The use of clarified thin stillage in biomass enzyme hydrolysis resulted in approximately 45 percent yield increase. The results are shown in FIG. 8.

Example 2

Figure 9:
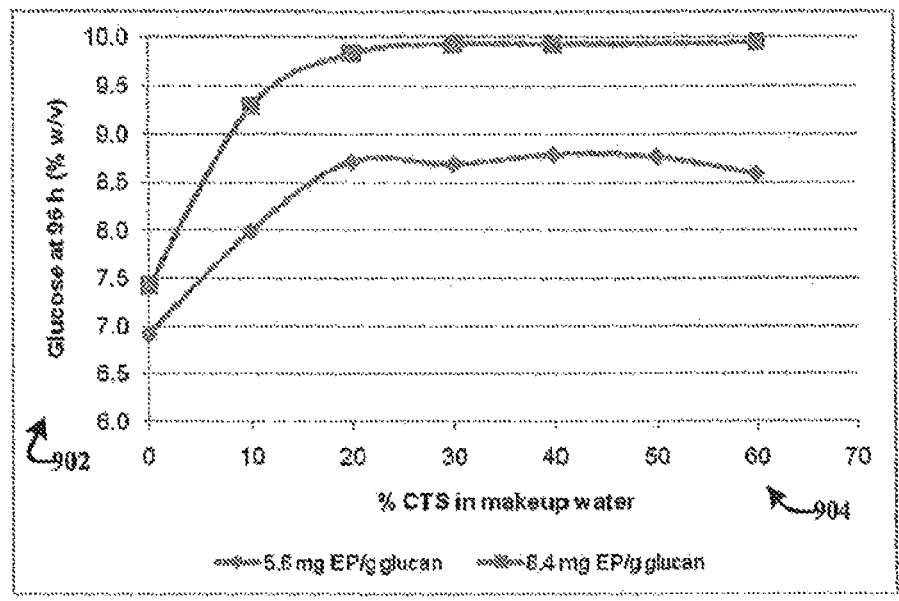
FIG. 9 is a graph of the results of biomass hydrolysis with a clarified thin stillage additive agent, according to an exemplary embodiment.

In the second example, a dose response study for determining the optimum level of clarified thin stillage (CTS) use in saccharification was conducted at two enzyme dosages: 5.6 and 8.4 mg of cellulase containing enzyme formulation per gram glucan. Ctec2 enzyme was used. The clarified thin stillage was used at 0 (control), 10, 20, 30, 40, 50, and 60% of the water makeup in the 15% total solids slurry. The saccharification was run for 96 h at 50° C., initial pH of 5.5 followed by a 48 h to 72 h fermentation at 32° C., initial pH of 5.5. Results of the total glucose (% w/v) 902 is plotted against the concentration of the Clarified Thin Stillage (CTS) 904 used in the water makeup, as shown in the example plot of FIG. 9.

The results again indicate that the use of clarified thin stillage significantly improved glucose yield in the saccharification process. Further, the results from this SHF study showed only slight differences in glucose production from CTS addition between 20 and 60% of the total water as observed for both the tested enzyme doses.

Example 3

In the third example experiment, following the 96 h enzymatic hydrolysis, the reactors were cooled to 32 degrees Celsius and the pH adjusted back up to 5.5. Urea was added at 0.06 g/L (as a nitrogen source) and Lactoside247 was added at 5 ppm. Yeast was inoculated at 0.5 g (dry)/L. The fermentations were carried out for up to 72 hours. Measurements of residual glucose levels were collected after 24 hours.

Figure 10:
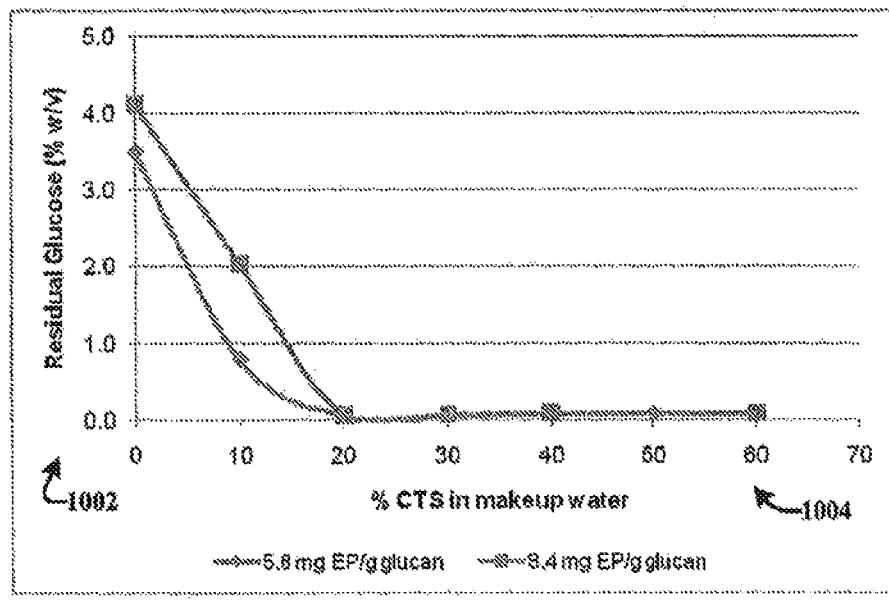
FIG. 10 is a graph of the residual glucose after fermentation of biomass subjected to hydrolysis with varying levels of a clarified thin stillage additive agent, according to an exemplary embodiment.

The residual glucose after 24 hours of fermentation 1002 was then plotted against the percent of CTS in the makeup water, as shown in example FIG. 10. Interestingly, the fermentation in reactors that had CTS in the makeup from 20%-60% of the water completed in 24 h (i.e. substantially all residual starch was consumed). Whereas with no CTS added, it took 72 h for the fermentation to complete even with the low sugar present in the reactor (not illustrated).

The ethanol produced in 24 h was over 70% of theoretical from glucan or over 80% of theoretical maximum from glucan at the 5.6 mg EP/g glucan and 8.4 mg EP/g glucan, respectively. These ethanol yields were obtained when CTS was used at 20-60% of the water in the makeup. With no CTS added during saccharification, the final ethanol produced after 72 h of fermentation was 56% and 60% of the theoretical maximum from glucan at the two enzyme dosages tested, respectively. Thus, it appears that the addition of the lignin binding agent not only increases enzyme conversion of cellulose to glucose, but also increases fermentation efficiency.

Example 4

In the fourth example experiment, a study was conducted to identify the optimum dose for the AnMBR effluent in enzymatic hydrolysis. For this example experiment, 5.8 mg enzyme per gram of glucan dose was tested. Again, Ctec2 enzyme was used. The AnMBR effluent was used at 0 (Control), 15, 30, 45, and 60% of the water makeup in the 15% total solids slurry. The saccharification was run for 115 h at 50 degrees Celsius, initial pH of 5.5 followed by 47 h fermentation at 32 degrees Celsius, initial pH of 5.5.

Figure 11:
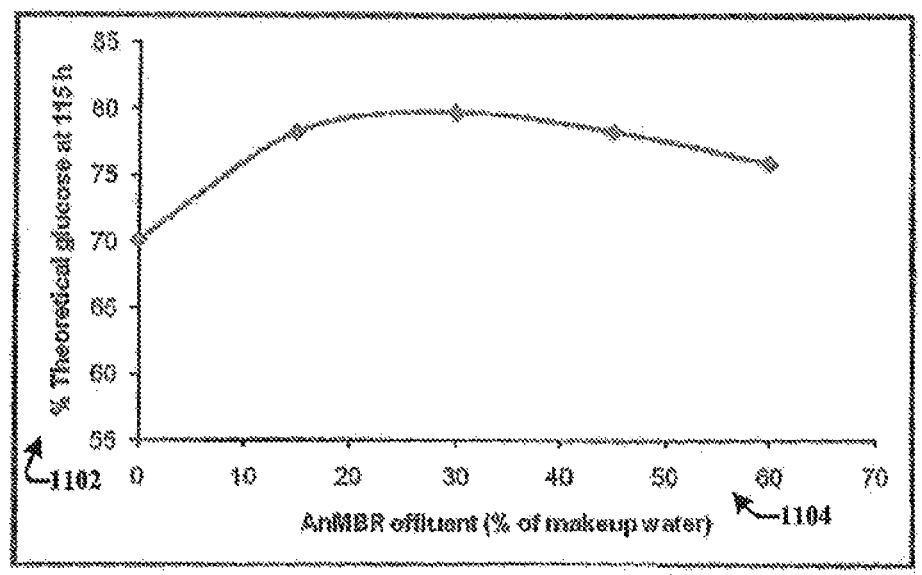
FIG. 11 is a graph of the results of biomass hydrolysis with an anaerobic membrane bioreactor effluent additive agent, according to an exemplary embodiment.

The percent of theoretical yield of glucose 1102 after the 115 hours of saccharification dependent upon percent AnMBR effluent makeup 1104 for this experiment is illustrated at FIG. 11. The results showed that the AnMBR effluent when added at 30% of the total makeup water produced the maximum glucose. This suggests that the AnMBR effluent can be used as a viable efficiency-enhancing agent in the saccharification of lignocellulosic C6 solids.

One advantage of using AnMBR effluent as an efficiency-enhancing agent is that the use of the AnMBR effluent stream maintains the process water balance. While thin stillage is a viable option, as noted above, the use of AnMBR effluent does not require transfer of water from the corn grain ethanol plant to the cellulosic plant. In addition to simplifying the water balance, the use of AnMBR effluent over thin stillage, or most other agents, avoids the potential for cross contamination between the cellulose plant and the corn grain ethanol plant.

Example 5

In the fifth example experiment, following the 115 h enzymatic hydrolysis, the reactors were cooled to 32 degrees Celsius and the pH adjusted back up to 5.5. Urea was added at 0.06 g/L (as a nitrogen source) and Lactoside247 was added at 5 ppm. Yeast was inoculated at 0.5 g (dry)/L. The fermentations were carried out for 47 hours. Measurements for residual glucose were collected from the samples at 24 and 47 hours.

Figure 12:
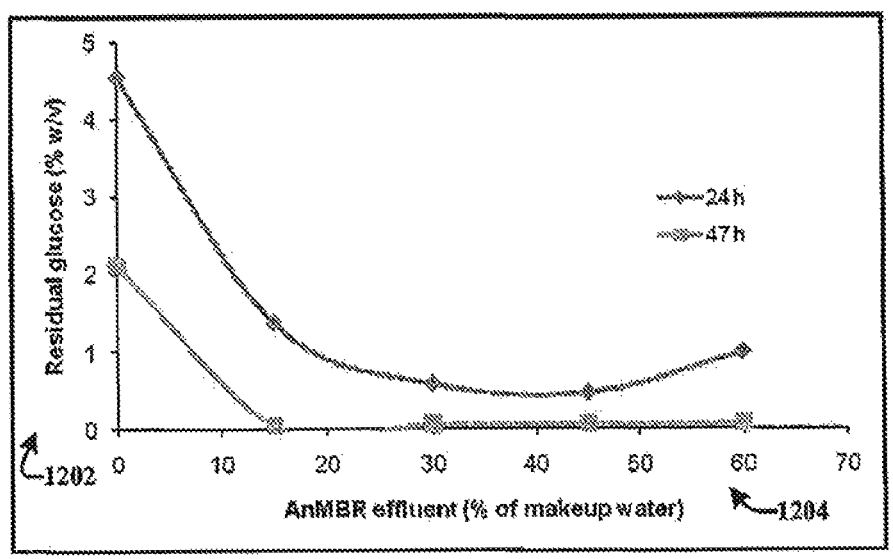
FIG. 12 is a graph of the residual glucose after fermentation of biomass subjected to hydrolysis with varying levels of an anaerobic membrane bioreactor effluent additive agent, according to an exemplary embodiment.

The residual glucose 1202 after 24 and 47 hours of fermentation was then plotted against the percent of AnMBR effluent 1204 in the makeup water, as shown in example FIG. 12. Interestingly, the fermentation in reactors that had AnMBR effluent in the makeup from 15%-60% of the water completed in 47 hours (i.e. substantially all residual starch was consumed). Whereas with no AnMBR effluent added, after 47 hours there was still residual sugar in the fermentation tank. Again, it appears that the addition of the lignin binding agent not only increases enzyme conversion of cellulose to glucose, but also increases fermentation efficiency.

Example 6

In the sixth example experiment, an experiment was performed to determine whether the combination of Clarified Thin Stillage (CTS) with Anaerobic Membrane Bioreactor (AnMBR) effluent provides additional efficiency improvements to the hydrolysis of the C6 solids. Here a 3 (CTS levels)×4 (AnMBR effluent levels) full factorial experiment was conducted to assess the interaction effect, if any, between the two additives. The CTS (clarified thin stillage) levels were 0, 10, and 25% of the total water in the makeup and the AnMBR effluent levels were 0, 10, 20, and 30% of the total water in the makeup. The enzyme Ctec2 from Novozymes was used at a dose of 6 mg protein per gram of glucan. A 15% total solids saccharification was run for 120 hours. The results of the experiment are illustrated at example FIG. 13.

The results indicate that there is an interaction effect observed between CTS and AnMBR effluent when used in combination to aid the saccharification of lignocellulosic C6 solids. It appears that the maximum glucose production (80.2% glucan to glucose conversion) was observed when CTS and AnMBR effluent are used at 10% each of the total makeup water, in this embodiment. However, using AnMBR effluent at 30% total makeup water helps with the water balance in the production facility in addition to giving good glucan-to-glucose conversion of roughly 79%. Thus, depending upon water load requirements, it may be beneficial to modify the composition of the makeup water to optimize plant operations while simultaneously improving efficiency of the hydrolysis of the C6 solids.

* * *

The embodiments as disclosed and described in the application (including the FIGURES and Examples) are intended to be illustrative and explanatory of the disclosed aspects. Modifications and variations of the disclosed embodiments, for example, of the apparatus and processes employed (or to be employed) as well as of the compositions and treatments used (or to be used), are possible; all such modifications and variations are intended to be within the scope of the one or more aspects.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

What is claimed is:

1. A method for treating lignocellulosic biomass to be supplied to a fermentation system for production of a fermentation product comprising:
   pre-treating the biomass into pre-treated biomass;
   separating the pre-treated biomass into a liquid component comprising sugars and a solids component comprising cellulose and lignin;
   treating the solids component of the pre-treated biomass into a treated component; and
   digesting lignin cake in an anaerobic membrane bioreactor to produce an anaerobic membrane bioreactor liquid effluent composition;
   wherein the biomass comprises lignocellulosic material;
   wherein treating the solids component comprises application of an enzyme formulation and a makeup water to form a slurry;
   wherein the enzyme formulation comprises a cellulase enzyme; wherein the makeup water comprises a protein source that is different from the cellulase enzyme;
   wherein the makeup water comprises the anaerobic membrane bioreactor liquid effluent composition, and wherein the lignocellulosic biomass comprises corn cobs and/or corn stover.

2. The method of claim 1, wherein the treating the solids component comprises releasing sugar.

3. The method of claim 2, wherein the sugars comprise glucose.

4. The method of claim 1, wherein the makeup water further comprises corn germ steep liquor and/or a corn kernel-based fermentation product.

5. The method of claim 4, wherein the corn kernel-based fermentation product comprises beer, whole stillage, thin stillage, clarified thin stillage, wet cake, syrup, backset, dried distillers grains, and combinations thereof.

6. The method of claim 5, wherein the corn kernel-based fermentation product is thin stillage.

7. The method of claim 5, wherein the corn kernel-based fermentation product is clarified thin stillage.

8. The method of claim 7, wherein the clarified thin stillage comprises at least 1 percent of the makeup water.

9. The method of claim 7, wherein a glucose yield is at least 60 percent of theoretically available glucose.

10. The method of claim 1, wherein the anaerobic membrane bioreactor effluent composition comprises at least 1 percent of the makeup water.

11. The method of claim 10, wherein a glucose yield is at least 90 percent of theoretically available glucose.

12. The method of claim 1, wherein the anaerobic membrane bioreactor effluent composition comprises about 30 to 70 percent of the makeup water.

13. The method of claim 1, wherein a glucose yield is at least 60 percent of theoretically available glucose.

14. The method of claim 1, wherein the slurry has a solids content of about 5 to 25 percent.

15. The method of claim 1, wherein the slurry has a pH of about 4.8 to 6.2.

16. The method of claim 1, wherein the treating the solids component further comprises holding the slurry at a temperature of about 30 to 60 degrees Celsius.

17. The method of claim 1, wherein the treating the solids component further comprises treating the solids component for about 48 to 144 hours.

18. The method of claim 1, wherein the pre-treating of the biomass further comprises steeping, and wherein the steeping comprises mixing the biomass with water to reach at least 10 percent solids content and applying sulfuric acid to the biomass in a concentration of about 0.8 to 1.3 percent by weight, and holding the biomass at a temperature of about 130 to 180 degrees Celsius for about 5 to 12 minutes.

19. The method of claim 18, wherein the pre-treating of the biomass further comprises steam explosion, and wherein the steam explosion comprises (a) holding the steeped biomass at a temperature of about 150 to 165 degrees Celsius and a pressure of about 75 to 125 pounds per square inch and (b) releasing the pressure.

20. The method of claim 1, wherein the lignocellulosic material comprises corn cobs, corn plant husks, corn plant leaves and corn stalks, wherein the corn cobs comprise about 25 to 50 percent of the lignocellulosic material, the corn plant husks and corn plant leaves comprise about 30 to 60 percent of the lignocellulosic material, and the corn stalks comprise about 10 to 30 percent of the lignocellulosic material.

* * * * *